US012569495B2

(12) United States Patent
Tang et al.

(10) Patent No.: US 12,569,495 B2
(45) **Date of Patent: *Mar. 10, 2026**

(54) INHIBITORS OF PORCINE REPRODUCTIVE AND RESPIRATORY SYNDROME VIRUS

(71) Applicants: UNIVERSITY OF CONNECTICUT, Farmington, CT (US); ATOMWISE INC., San Francisco, CA (US)

(72) Inventors: Young Tang, Storrs, CT (US); Antonio E. Garmendia, Storrs, CT (US); Chang Huang, Storrs, CT (US); Denzil Bernard, San Francisco, CA (US)

(73) Assignees: UNIVERSITY OF CONNECTICUT, Farmington, CT (US); ATOMWISE INC., San Francisco, CA (US)

( * ) Notice: Subject to any disclaimer, the term of this patent is extended or adjusted under 35 U.S.C. 154(b) by 602 days.

This patent is subject to a terminal disclaimer.

(21) Appl. No.: 17/999,275

(22) PCT Filed: May 28, 2021

(86) PCT No.: PCT/US2021/034707

§ 371 (c)(1),
(2) Date: Nov. 18, 2022

(87) PCT Pub. No.: WO2021/243118

PCT Pub. Date: Dec. 2, 2021

(65) Prior Publication Data

US 2023/0241074 A1 Aug. 3, 2023

Related U.S. Application Data

(60) Provisional application No. 63/031,631, filed on May 29, 2020.

(51) Int. Cl.

| | |
|---|---|
| *A61K 31/5377* | (2006.01) |
| *A61K 31/498* | (2006.01) |
| *A61P 31/14* | (2006.01) |

(52) U.S. Cl.

CPC ........ *A61K 31/5377* (2013.01); *A61K 31/498* (2013.01); *A61P 31/14* (2018.01)

(58) Field of Classification Search

None

See application file for complete search history.

(56) References Cited

U.S. PATENT DOCUMENTS

| | | | |
|---|---|---|---|
| 8,889,664 | B2 | 11/2014 | Bajalieh et al. |
| 9,011,863 | B2 | 4/2015 | Aftab et al. |

(Continued)

FOREIGN PATENT DOCUMENTS

| | | | |
|---|---|---|---|
| BR | 112017017229 | B1 | 8/2023 |
| CN | 103525775 | A | 1/2014 |

(Continued)

OTHER PUBLICATIONS

Honkanen et. al. "Prognostic and predictive role of tumour-associated macrophages in HER2 positive breast cancer" Scientific Reports, Sep. 2019, 10961, 1-9. DOI: 10.1038/s41598-019-47375-2 (Year: 2019).*

(Continued)

*Primary Examiner* — Jennifer A Berrios
*Assistant Examiner* — Sophia Reilly
(74) *Attorney, Agent, or Firm* — Michael Best & Friedrich LLP

(57) ABSTRACT

Disclosed herein are compositions comprising a compound of Formula (I) and methods for treating or prophylaxis of porcine reproductive and respiratory syndrome (PRRS) therewith (I).

(Continued)

B7

B7-A1

B7-A2

B7-A3

B7-A4

B7-A5

B7-A6

(I)

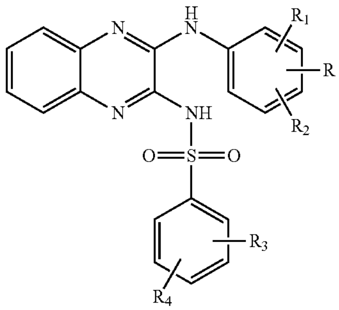

3 Claims, 19 Drawing Sheets

Specification includes a Sequence Listing.

(56) References Cited

U.S. PATENT DOCUMENTS

| | | | |
|---|---|---|---|
| 2003/0003112 | A1 | 1/2003 | Audonnet et al. |
| 2009/0163545 | A1 | 6/2009 | Goldfarb |
| 2010/0087440 | A1 | 4/2010 | Bajjalieh et al. |

FOREIGN PATENT DOCUMENTS

| | | | |
|---|---|---|---|
| WO | 2009017838 | A2 | 2/2009 |
| WO | 2012006552 | A1 | 1/2012 |
| WO | 2012065057 | A2 | 5/2012 |
| WO | 2014148738 | A1 | 9/2014 |
| WO | 2015153959 | A2 | 10/2015 |
| WO | 2016135053 | A1 | 9/2016 |
| WO | 2018073237 | A1 | 4/2018 |
| WO | 2021068533 | A1 | 4/2021 |

OTHER PUBLICATIONS

Paulekuhn, G. S. et al. "Trends in active pharmaceutical ingredient salt selection based on analysis of the orange book database." Journal of medicinal chemistry 50.26 (2007): 6665-6672.

Bass, A. S., et al. Exploratory drug safety: a discovery strategy to reduce attrition in development. J Pharmacol Toxicol Methods 60, 69-78, (2009).

Benfield DA, et al. Characterization of swine infertility and respiratory syndrome (SIRS) virus (isolate ATCC VR-2332). Journal of veterinary diagnostic investigation : official publication of the American Association of Veterinary Laboratory Diagnosticians, Inc. 1992;4(2):127-33.

Briz V, et al. HIV entry inhibitors: mechanisms of action and resistance pathways. J Antimicrob Chemother. 2006;57 (4):619-27.

Burkard C, et al. Pigs Lacking the Scavenger Receptor Cysteine-Rich Domain 5 of CD163 Are Resistant to Porcine Reproductive and Respiratory Syndrome Virus 1 Infection. Journal of virology. 2018;92(16).

Burkard C, et al. Precision engineering for PRRSV resistance in pigs: Macrophages from genome edited pigs lacking CD163 SRCR5 domain are fully resistant to both PRRSV genotypes while maintaining biological function. PLoS Pathog. 2017;13(2):e1006206.

C.T.F.A. Cosmetic Ingredient Handbook, 1992, pp. 587-592.

Calvert JG, et al. CD163 expression confers susceptibility to porcine reproductive and respiratory syndrome viruses. J Virol. 2007;81(14):7371-9.

Cavanagh D. Nidovirales: a new order comprising Coronaviridae and Arteriviridae. Archives of virology. 1997;142(3):629-33.

Das PB, et al. The minor envelope glycoproteins GP2a and GP4 of porcine reproductive and respiratory syndrome virus interact with the receptor CD163. J Virol. 2010;84(4):1731-40.

Delrue I, et al. Susceptible cell lines for the production of porcine reproductive and respiratory syndrome virus by stable transfection of sialoadhesin and CD163. BMC biotechnology. 2010;10:48.

Delwatta, S. L., et al. Reference values for selected hematological, biochemical and physiological parameters of Sprague-Dawley rats at the Animal House, Faculty of Medicine, University of Colombo, Sri Lanka. Animal Model Exp Med 1, 250-254 (2018).

Guo C, et al. Highly Efficient Generation of Pigs Harboring a Partial Deletion of the CD163 SRCR5 Domain, Which Are Fully Resistant to Porcine Reproductive and Respiratory Syndrome Virus 2 Infection. Front Immunol. 2019; 10:1846.

Halbur PG. PRRS Plus—PRRS Virus Infection in Combination with Other Agents. hypothesis. 1998;1997:1998b-2000 (7 pages).

He, Q., et al. Sex-specific reference intervals of hematologic and biochemical analytes in Sprague-Dawley rats using the nonparametric rank percentile method. PloS one 12, e0189837 (2017).

Hsieh CH, et al. Miro1 Marks Parkinson's Disease Subset and Miro1 Reducer Rescues Neuron Loss in Parkinson's Models. Cell Metab. 2019;30(6):1131-40 e7.

Huang, C., et al. "Small molecules block the interaction between porcine reproductive and respiratory syndrome virus and CD163 receptor and the infection of pig cells." Virology Journal 17.1 (2020): 1-11.

International Preliminary Report on Patentability for Application No. PCT/US2021/034707 dated Nov. 17, 2022 (7 pages).

International Search Report and Written Opinion for Application No. PCT/US2021/034707 dated Nov. 3, 2021 (15 pages).

Kaneko M, et al. A Novel Tricyclic Polyketide, Vanitaracin A, Specifically Inhibits the Entry of Hepatitis B and D Viruses by Targeting Sodium Taurocholate Cotransporting Polypeptide. J Virol. 2015;89(23):11945-53.

Kaneko M, et al. Chemical array system, a platform to identify novel hepatitis B virus entry inhibitors targeting sodium taurocholate cotransporting polypeptide. Sci Rep. 2018;8(1):2769.

Kodama Y, et al. An improved bimolecular fluorescence complementation assay with a high signal-to-noise ratio. Biotechniques. 2010;49(5):793-805.

Kuritzkes DR. HIV-1 entry inhibitors: an overview. Curr Opin HIV AIDS. 2009;4(2):82-7.

Lee YJ, et al. Generation of a porcine alveolar macrophage cell line for the growth of porcine reproductive and respiratory syndrome virus. J Virol Methods. 2010;163(2):410-5.

Ma H, et al. The Crystal Structure of the Fifth Scavenger Receptor Cysteine-Rich Domain of Porcine CD163 Reveals an Important Residue Involved in Porcine Reproductive and Respiratory Syndrome Virus Infection. Journal of virology. 2017;91(3) e01897-16.

McCutcheon's vol. 1, Emulsifiers & Detergents, 1994, North American Edition, pp. 236-239.

Meng XJ. Heterogeneity of porcine reproductive and respiratory syndrome virus: implications for current vaccine efficacy and future vaccine development. Veterinary microbiology. 2000;74(4):309-29.

Modern Pharmaceutics, Chapters 9 and 10, Banker & Rhodes, eds. (1979).

Murtaugh MP, et al. Immunological responses of swine to porcine reproductive and respiratory syndrome virus infection. Viral immunology. 2002;15(4):533-47.

Murtaugh MP, et al. The ever-expanding diversity of porcine reproductive and respiratory syndrome virus. Virus research. 2010;154(1-2):18-30.

Music N, et al. The role of porcine reproductive and respiratory syndrome (PRRS) virus structural and non-structural proteins in virus pathogenesis. Animal health research reviews / Conference of Research Workers in Animal Diseases. 2010;11(2):135-63.

Nan Y, et al. Improved Vaccine against PRRSV: Current Progress and Future Perspective. Front Microbiol. 2017;8:1635.

National Center for Biotechnology Information (2023). PubChem Compound Summary for CID 3995716. Retrieved Jan. 30, 2023 from https://pubchem.ncbi.nlm.nih.gov/compound/3995716 (13 pages).

(56) References Cited

OTHER PUBLICATIONS

Nkongolo S, et al. Cyclosporin A inhibits hepatitis B and hepatitis D virus entry by cyclophilin-independent interference with the NTCP receptor. J Hepatol. 2014;60(4):723-31.
Prather RS, et al. An intact sialoadhesin (Sn/SIGLEC1/CD169) is not required for attachment/internalization of the porcine reproductive and respiratory syndrome virus. J Virol. 2013;87(17):9538-46.
Qian K, Morris-Natschke SL, Lee KH. HIV entry inhibitors and their potential in HIV therapy. Med Res Rev. 2009;29(2):369-93.
Reed, L.J. et al. "A simple method of estimating fifty per cent endpoints." American journal of epidemiology 27.3 (1938): 493-497.
Remington's Pharmaceutical Sciences, 15th Ed. 1975, pp. 335-337.
Tian K, et al. Emergence of fatal PRRSV variants: unparalleled outbreaks of atypical PRRS in China and molecular dissection of the unique hallmark. PLoS One. 2007;2(6):e526.
Van Gorp H, et al. Identification of the CD163 protein domains involved in infection of the porcine reproductive and respiratory syndrome virus. J Virol. 2010;84(6):3101-5.
Wallach I, et al. AtomNet: a deep convolutional neural network for bioactivity prediction in structure-based drug discovery. arxivorg. 2015;arXiv preprint arXiv:1510.02855.
Wang XJ, et al. Irbesartan, an FDA approved drug for hypertension and diabetic nephropathy, is a potent inhibitor for hepatitis B virus entry by disturbing Na(+)-dependent taurocholate cotransporting polypeptide activity. Antiviral Res. 2015;120:140-6.
Wang, X., et al. "Role of phosphatidylinositol 3-kinase (PI3K) and Akt1 kinase in porcine reproductive and respiratory syndrome virus (PRRSV) replication." Archives of virology 159 (2014): 2091-2096.
Watashi K, et al. Cyclosporin A and its analogs inhibit hepatitis B virus entry into cultured hepatocytes through targeting a membrane transporter, sodium taurocholate cotransporting polypeptide (NTCP). Hepatology. 2014;59(5):1726-37.
Wei Z, et al. Influence of N-linked glycosylation of minor proteins of porcine reproductive and respiratory syndrome virus on infectious virus recovery and receptor interaction. Virology. 2012;429(1):1-11.
Weingartl HM, et al. Continuous porcine cell lines developed from alveolar macrophages: partial characterization and virus susceptibility. J Virol Methods. 2002;104(2):203-16.
Wells KD, et al. Replacement of Porcine CD163 Scavenger Receptor Cysteine-Rich Domain 5 with a CD163-Like Homolog Confers Resistance of Pigs to Genotype 1 but Not Genotype 2 Porcine Reproductive and Respiratory Syndrome Virus. J Virol. 2017;91(2) e01521-16.
Whitworth KM, et al. Gene-edited pigs are protected from porcine reproductive and respiratory syndrome virus. Nat Biotechnol. 2016;34(1):20-2.
Zimmerman JJ, et al. General overview of PRRSV: a perspective from the United States. Veterinary microbiology. 1997;55(1-4):187-96.
Chinese National Intellectual Propery Administration. Notification of First Office Action for Application No. 202180038600.5, dated Apr. 7, 2024 (27 pages with translation).
European Patent Office. Extended European Search Report for Application No. 21812899.9, dated Apr. 23, 2024 (18 pages).
Database Registry (CHEMCATS) [Online] Mar. 19, 2001 (Mar. 19, 2001), Database Accession No. 328039-82-3 (1 page).
Database Registry (Enamine) [Online] Mar. 19, 2001 (Mar. 19, 2001), Database Accession No. 328039-44-7 (1 page).
Database Registry (CHEMCATS) [Online] Jul. 25, 2003 (Jul. 25, 2003), Database Accession No. 554424-44-1 (1 page).
Database Registry (CHEMCATS) [Online] Aug. 5, 2003 (Aug. 5, 2003), Database Accession No. 560995-89-3 (1 page).
Database Registry (CHEMCATS) [Online] Aug. 12, 2003 (Aug. 12, 2003), Database Accession No. 565172-27-2 (1 page).
Database Registry (Enamine) [Online] Aug. 13, 2004 (Aug. 13, 2004), Database Accession No. 726160-73-2 (1 page).
Database Registry (CHEMCATS) [Online] Sep. 2, 2004 (Sep. 2, 2004), Database Accession No. 737816-04-5 (1 page).
Brinton, M. A., et al. "Arteriviruses." Encyclopedia of Virology (2008): 176.
Murtaugh, M.P. et al. "Immunological solutions for treatment and prevention of porcine reproductive and respiratory syndrome (PRRS)." Vaccine 29.46 (2011): 8192-8204.
Miller, K. E., et al. "Bimolecular fluorescence complementation (BiFC) analysis: advances and recent applications for genome-wide interaction studies." Journal of molecular biology 427.11 (2015): 2039-2055.

* cited by examiner

B7

B7-A1

B7-A2

B7-A3

B7-A4

B7-A5

B7-A6

B7-A7

B7-A8

INHIBITORS OF PORCINE REPRODUCTIVE AND RESPIRATORY SYNDROME VIRUS

CROSS-REFERENCE TO RELATED APPLICATIONS

This application is a U.S. national stage entry of International Patent Application No. PCT/US2021/034707, filed on May 28, 2021, which claims priority to U.S. Provisional Patent Application No. 63/031,631, filed on May 29, 2020, the entire contents of each of which are fully incorporated herein by reference.

FEDERALLY SPONSORED RESEARCH

This invention was made with government support under grant number 2017-67016-26675 awarded by the U.S. Department of Agriculture/National Institute of Food and Agriculture. The government has certain rights in the invention.

REFERENCE TO SEQUENCE LISTING

This application is filed with a Computer Readable Form of a Sequence Listing in accord with 37 C.F.R. § 1.821(c). The text file submitted by EFS-Web, "209670-9042-US02_sequence_listing_17-NOV-2022_ST25.txt," was created on Nov. 17, 2022, contains 10 sequences, has a file size of 2.18 Kbytes, and is hereby incorporated by reference in its entirety.

TECHNICAL FIELD

Described herein are compositions and methods for treating or prophylaxis of porcine reproductive and respiratory syndrome (PRRS) and in particular, inhibiting the PRRS virus by targeting porcine CD163-SRCR5.

BACKGROUND

Porcine reproductive and respiratory syndrome (PRRS) is one of the most economically significant swine diseases, with over billion-dollar losses to the global pork industry annually. The causative virus of PRRS (PRRSV) is an enveloped, positive-sense, single-stranded RNA virus of the Arterivirus genus within the order Nidovirales. PRRSV infection results in severe reproductive failure in sows and respiratory disease in piglets. This may be complicated by secondary infections with even greater clinical manifestations and mortality. Unfortunately, due to the high genetic and antigenic heterogeneity of PRRSV, broadly effective vaccines are still lacking. New approaches are needed to combat the PRRS panzootic to mitigate the devastating consequences of this disease.

The productive PRRSV infection occurs primarily through porcine alveolar macrophages (PAMs) in the pig lung. CD163, a macrophage-specific membrane scavenger receptor, is a key receptor for PRRSV infection. The necessity of CD163 expression for PRRSV infection was confirmed by knockout studies showing pigs without CD163 become PRRSV-resistant. Out of the 9 extracellular scavenger receptor cysteine rich (SRCR) domains in CD163, SRCR5 was found crucial for PRRSV infection, and monocytes/macrophages from pigs expressing CD163 with deleted SRCR5 are fully protected from PRRSV infection. Cellular pull-down assay and bimolecular fluorescence complementation (BiFC) analysis revealed that PRRSV directly interacts with CD163 via its minor glycoproteins GP2a and GP4, which bind the CD163 extracellular but not transmembrane or cytoplasmic region. Thus, it is reasonable to assume that the CD163-SRCR5 domain directly interacts with the PRRSV glycoproteins. However, assays studying protein-protein interactions (PPIs) between the CD163-SRCR5 domain and PRRSV glycoproteins have not been reported.

A number of small molecules have been identified to effectively block the entry of various human viruses by binding and antagonizing the host cell receptors/co-receptors. However, a small molecule targeting protein-protein interactions (PPI) between PRRSV and CD163 has not been reported. A recent study of the porcine CD163 X-ray crystal structure revealed a distinct 3-D structural arrangement of the CD163-SRCR5 domain loop 5-6 region (Phe 544-Arg 570) compared to its homologous region in SRCR-superfamily proteins M2BP and CDS. Furthermore, a CD163 mutant with Arg 561 changed to Ala in the loop 5-6 region of SRCR5 inhibited PRRSV infection compared with the wild type CD163.

Therefore, there is a need for targeting pig CD163-SRCR5 at the Arg 561 region to prevent PRRSV infection.

SUMMARY

Disclosed herein are antiviral compositions and methods for treating subjects with such compositions.

In one aspect, described herein are methods for treating a reproductive respiratory syndrome by administering to a subject in need thereof an effective amount of a compound of Formula I:

(I)

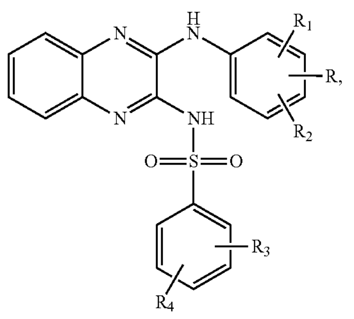

wherein:

R is

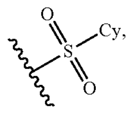

where Cy is 6- or 5-membered heterocyclylene or $C_{3-6}$ cycloalkylene, wherein Cy is unsubstituted or substituted with 1-6 substituents independently selected from $C_{1-4}$ alkyl, $C_{1-2}$ fluoroalkyl, or halogen;

$R^1$ and $R^2$ are each independently hydrogen, $C_{1-4}$ alkyl, $C_{1-2}$ fluoroalkyl, cyano, or halogen; and $R^3$ and $R^4$ are different or the same, wherein $R^3$ and $R^4$ are each independently $C_{1-4}$ alkyl, halogen, hydrogen, $C_{1-2}$ fluoroalkyl, or cyano.

In some embodiments, R is

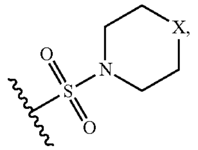

where X is O, NH, or $CH_2$. In another aspect, the reproductive respiratory syndrome comprises one or more of the following symptoms: fever; lethargy; loss of appetite; vomiting; cough; sneezing; wheezing; labored breathing; high blood pressure; low blood pressure; respiratory distress; depression; cyanosis of the ears, abdomen, or vulva, stillbirths, premature births; abortions; postweaning respiratory diseases; pulmonary edema, or cardiac arrest. In some embodiments, decreased function of pulmonary alveolar and intravascular macrophages causes the reproductive respiratory syndrome. In some embodiments, the compound of Formula I is administered to the subject prior to, during, and after infection with an arterivirus. In some embodiments, the compound of Formula I is administered to the subject after infection with an arterivirus. In another aspect, the subject is a mammal. In some embodiments, the subject is a pig. In another aspect, the administration is oral, nasal, topical, intravenous, subcutaneous, intramuscular, intravaginal, or intrarectal.

In another aspect, described herein are methods for inhibiting an interaction between scavenger receptor cysteine-rich domain 5 (SRCR5) of Cluster of Differentiation 163 (CD163) and glycoproteins of an arterivirus by administering to a subject in need thereof an effective amount of a compound of Formula I:

(I)

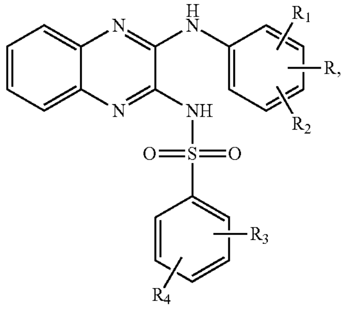

wherein:

R is

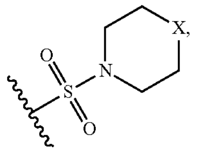

where X is O, NH, or $CH_2$; and $R^1$, $R^2$, $R^3$, and $R^4$ are each independently hydrogen, methyl, or halogen. In some embodiments, the arterivirus is porcine reproductive and respiratory syndrome virus (PRRSV). In some embodiments, the PRRSV is VR-2332, SDSU73, NADC30 (Type II), or Lelystad (Type I). In some embodiments, the glycoproteins comprise glycoprotein 2a precursor (GP2a) or glycoprotein 4 precursor (GP4). In some embodiments, the CD163 is expressed by monocytes or macrophages. In some embodiments, the compound of Formula I treats, ameliorates the symptoms of, or is prophylactic for an infection of the subject by the arterivirus. In some embodiments, the subject is a pig. In some embodiments, the arterivirus infects upper respiratory system, spleen, thymus, tonsils, lymph nodes, and Peyer's patches. In some embodiments, the compound of Formula I reduces viral titer by at least about 1.5 log.

In another aspect, described herein are methods for treating, ameliorating the symptoms of, prophylaxis of, or lessening the viral burden of a pig infected with an arterivirus comprising administering a therapeutically effective amount of a pharmaceutical composition comprising one or more pharmaceutically acceptable excipients and one or more compounds selected from:

(B7)

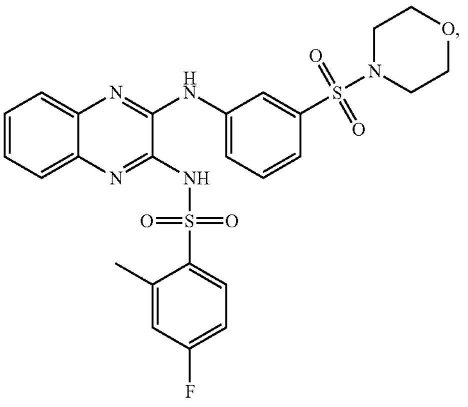

(B7-A1)

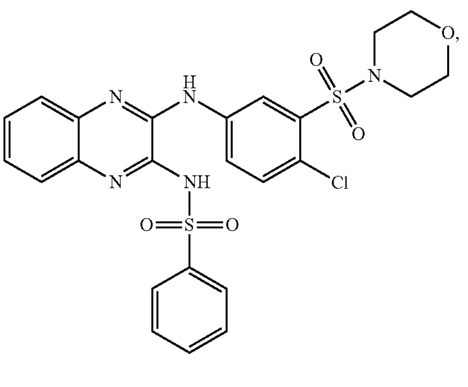

(B7-A2)

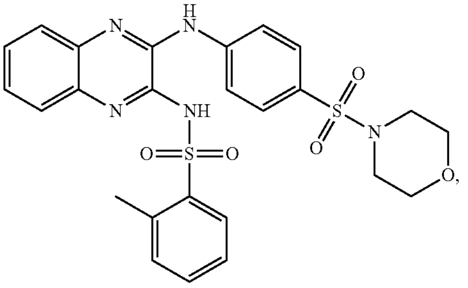

-continued (B7-A3)

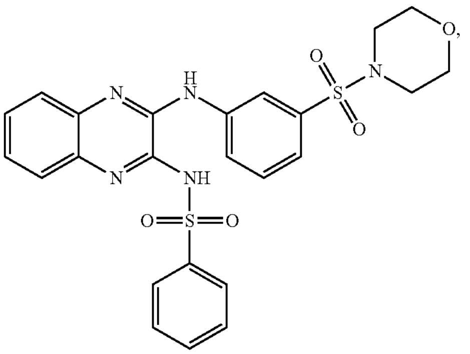

or (B7-A4)

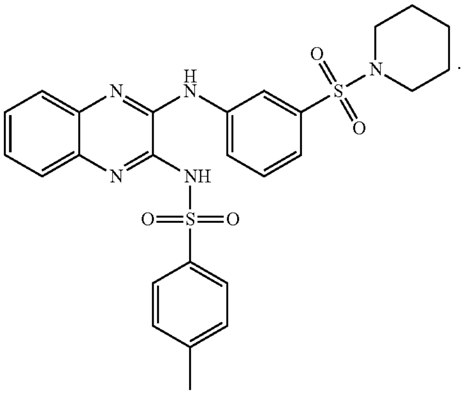

In some embodiments, one or more analgesics, anti-virals, anti-infectives, expectorants, decongestants, anti-fever, or other pharmaceutical agents are co-administered. In some embodiments, the therapeutically effective amount of the compounds is about 0.5 mg/kg to about 2.5 mg/kg.

In another aspect, described herein are pharmaceutical compositions comprising:

an effective amount of compound of Formula I:

(I)

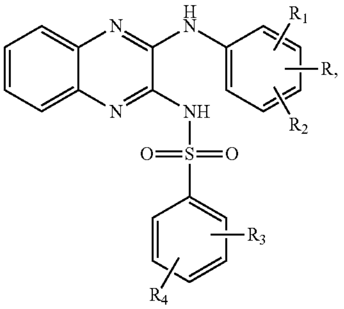

wherein:

R is

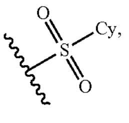

where Cy is 5- to 6-membered heterocyclylene or 03-6 cycloalkylene, wherein Cy is unsubstituted or substituted with 1-6 substituents independently selected from $C_{1-4}$ alkyl, $C_{1-2}$ fluoroalkyl, or halogen;

$R^1$ and $R^2$ are each independently hydrogen, $C_{1-4}$ alkyl, $C_{1-2}$ fluoroalkyl, cyano, or halogen;

$R^3$ and $R^4$ are each independently hydrogen, $C_{1-4}$ alkyl, $C_{1-2}$ fluoroalkyl, cyano, or halogen; with the proviso that:

when $R^3$ and $R^4$ are each hydrogen at least one of $R^1$ and $R^2$ is not hydrogen, where when one of $R^1$ or $R^2$ is hydrogen $R^2$ or $R^1$ is not chloro;

when $R^3$ or $R^4$ is methyl in the para-position R is not

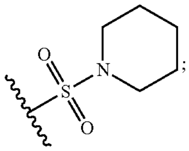 [SMILES: *S(=O)(=O)N1CCCCC1]

and when $R^3$ or $R^4$ is chloro in the para-position R is not

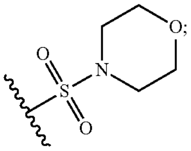 [SMILES: *S(=O)(=O)N1CCOCC1]

and one or more pharmaceutically acceptable excipients.

In some embodiments, R is

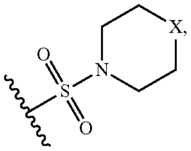

where X is O, NH, or $CH_2$.

In some embodiments, R is

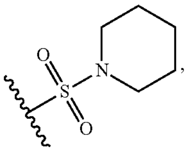

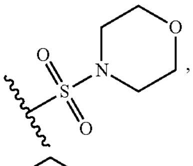

or

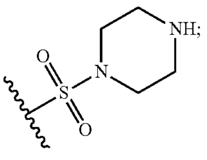

$R^1$ is hydrogen; and $R^2$, $R^3$, and $R^4$ are each independently hydrogen, methyl, or halogen.

In some embodiments, R is

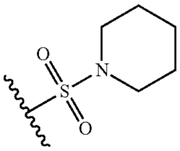
or
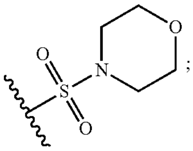
;

$R^1$ is hydrogen;
$R^2$ is hydrogen or halogen; and
$R^3$ and $R^4$ are each independently hydrogen, methyl, or halogen.

In some embodiments, R is

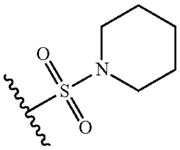
or
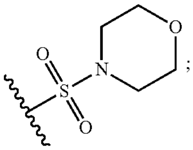
;

$R^1$ is hydrogen;
$R^2$ is halogen; and
$R^3$ and $R^4$ are each independently hydrogen, methyl, or halogen.

In some embodiments, the compound is one of Formula II, or III:

(II)

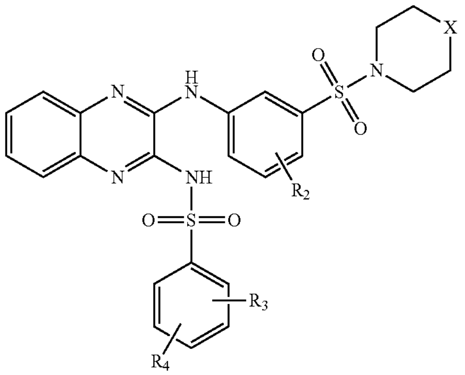
or (III)

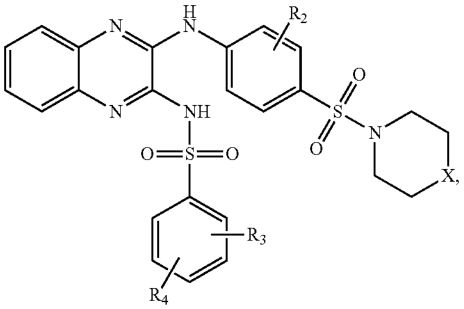
, wherein:
X is O, NH, or $CH_2$; and
$R^2$, $R^3$, and $R^4$ are each independently hydrogen, methyl, or halogen. In some embodiments, X is O. In some embodiments, X is $CH_2$. In some embodiments, X is NH. In some embodiments, $R^2$ is halogen or hydrogen. In another aspect, $R^2$ is chloro. In some embodiments, $R^2$ is hydrogen. In some embodiments, $R^3$ is hydrogen or methyl and $R^4$ is hydrogen or halogen. In some embodiments, $R^3$ is methyl and $R^4$ is halogen. In some embodiments, $R^3$ is hydrogen and $R^4$ is methyl. In some embodiments, $R^3$ is methyl and $R^4$ is fluoro. In another aspect, $R^3$ and $R^4$ are hydrogen. In some embodiments, the compound is selected from:

(B7)

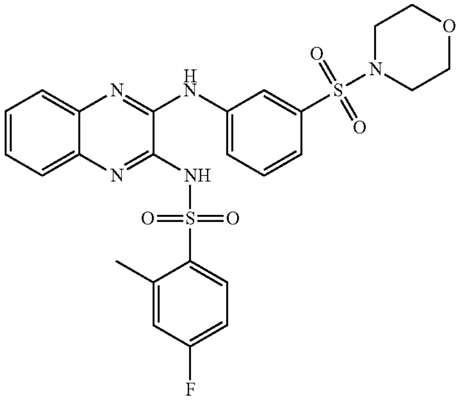
or (B7-A2)

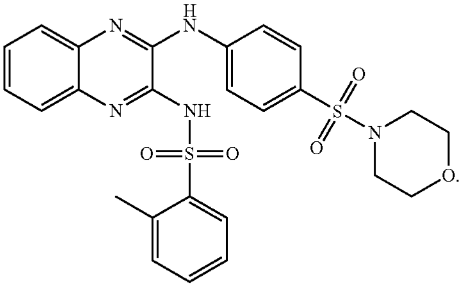
.

Also described herein are pharmaceutical compositions comprising: an effective amount of:

(B7)

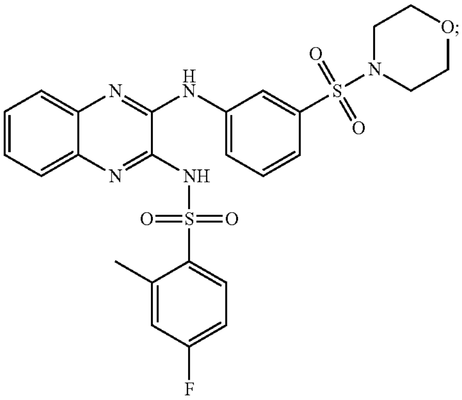
;

and one or more pharmaceutically acceptable excipients.

In some embodiments, the pharmaceutically acceptable excipients comprise buffering agents, solubilizers, solvents, antimicrobial preservatives, antioxidants, suspension agents, a tablet or capsule diluent, or a tablet disintegrant.

In some embodiments, the compound of Formula I inhibits an interaction between scavenger receptor cysteine-rich domain 5 (SRCR5) of Cluster of Differentiation 163 (CD163) and glycoproteins of an arterivirus. In another aspect, the compound of Formula I treats, ameliorates the symptoms of, or is prophylactic for an infection by an arterivirus. In another aspect, the composition comprises about 5 mg to about 400 mg of the compound of Formula I.

Also disclosed herein is a pharmaceutical dosage form comprising a therapeutically effective amount of the pharmaceutical composition described herein.

In one aspect, the therapeutically effective amount of the pharmaceutical composition comprises about 0.5 mg/kg to about 2.5 mg/kg of the compound of Formula I.

Also disclosed herein is the use of a pharmaceutical composition described herein or treating a reproductive respiratory syndrome by administering to a subject in need thereof an effective amount of the compound of Formula I.

Also disclosed herein is a kit comprising one or more dosage forms of the pharmaceutical composition described herein, further comprising one or more packages, receptacles, delivery devices, labels, or instructions for use.

Also disclosed herein is a method for screening for biologically active compounds capable of interacting with a porcine CD163-SRCR5 domain, the method comprising: (a) on a processor, performing an in silico artificial intelligence molecular screen to identify compounds capable of interacting with a porcine CD163-SRCR5 domain; and (b) testing the compounds identified in step (a) in a bimolecular fluorescence complementation (BiFC) assay for their ability to inhibit protein-protein interactions between the porcine CD163-SRCR5 domain and a GP2a or GP4. In some embodiments, the BiFC assay comprises transfecting cells with vectors expressing CD163-SRCR5 and GP2a or GP4, incubating the transfected cells with a quantity of a compound of interest, and evaluating the cells for protein-protein interactions between CD163-SRCR5 and GP2a or GP4 using fluorescence microscopy.

DESCRIPTION OF THE DRAWINGS

FIG. 1A shows a schematic of the BiFC assay fusion protein constructs between pig CD163 SRCRs or PRRSV minor envelope glycoproteins and the fragments of venus protein VN155(I152L) or VC155, respectively. FIG. 1B shows bright field and fluorescent images of HEK293T cells 24 hours after co-transfection of SRCR5-VN or SRCR2-VN plasmids with GP2a-VC. Bar=250 μm. The bar chart shows the relative cell fluorescence. Mean±SD. n=3. : p<0.01. FIG. 1C shows bright field and fluorescent images of HEK293T cells 24 hours after co-transfection of SRCR5-VN or SRCR2-VN plasmids with GP2a-VC. Bar=250 μm. The bar chart shows the relative cell fluorescence elative fluorescence intensity. Mean±SD, n=3, : p<0.01. FIG. 1D shows bright field and fluorescent images of the BiFC assay between SRCR5-VN and GP2a-VC proteins. Images showing positive inhibitory effect of compound B7 but not B8, with DMSO as the Ctrl. Bar=250 μm. The bar chart shows the relative fluorescence intensity. Mean±SD, n=3. The indicators "a," "b," and "ab" represent significant differences in sample means by Tukey post-hoc test after Anova analysis. Means are different if they do not share the same letter. FIG. 1E shows bright field and fluorescent images of the BiFC assay between SRCR5-VN and GP4-VC proteins showing similar inhibitory effect by B7 compound but not by B8. Bar=120 μm. The bar chart shows the relative fluorescence intensity. Mean±SD, n=3. The indicators "a" and "b" represent significant differences in sample means by Tukey post-hoc test after Anova analysis.

FIG. 5A shows qRT-PCR for PRRSV in total RNAs extracted from PRRSV strain VR-2332 infected PAMs treated with various concentrations of B7 compound. Values are normalized with GAPDH of PAMs. Mean±SD, n=3, *: p<0.001, n.s.: non-significant. FIG. 5B shows titration assay results for PRRSV in the culture media of PAMs treated as described in FIG. 5A. Bars=mean±SD, n=3, : p<0.01, *: p<0.001, n.s.: non-significant. FIG. 5C shows a qRT-PCR for PRRSV in total RNAs extracted from PAMs infected by different strains of PRRSV and treated with 15 μM of B7 compound. Values are normalized with GAPDH of PAMs. Bars=mean±SD, n=3, : p<0.01. FIG. 5D shows titration assay results for PRRSV in the culture media of PAMs treated as described in FIG. 5C. Bars=mean±SD, n=3, **: p<0.01.

FIG. 6A shows the molecular structures of B7 analogues (B7-A1 to B7-A6). FIG. 6B shows the BiFC assay between SRCR5-VN and GP2a-VC proteins. Representative fluorescent images showing different effects of compound B7 and its analogues on the protein-protein interactions between SRCR5/GP2a, with DMSO as the Ctrl. Bar=250 μm.

FIG. 7A shows the relative fluorescence intensity in FIG. 6B quantified by ImageJ. Mean±SD, n=3. : p<0.01, *: p<0.001. n.s.: non-significant. FIG. 7B shows qRT-PCR for PRRSV in total RNAs extracted from PRRSV strain VR-2332 infected PAMs treated with 15 μM of B7 and its analogues. Values are normalized with GAPDH of PAMs. Bars=mean±SD, n=3. *: p<0.05, **: p<0.01. FIG. 7C shows titration assay results for PRRSV in the culture media of PAMs treated as described in FIG. 7B. Bars=mean±SD, n=3, *: p<0.05, **: p<0.01, n.s.: non-significant.

FIG. 9A shows the molecular structures of B7-A7 and B7-A8. FIG. 9B shows titration assay results for the culture media of PAMs treated with B7, B7-A7, or B7-A8 and infected by PRRSV strain V-2332. Bars=mean±SD, n=3, ***: p<0.001, n.s.: non-significant. FIG. 9C shows qRT-PCR for PRRSV in total RNAs extracted from PAMs infected by PRRSV VR-2332 and treated with 15 μM of B7 compound at pre and/or post-inoculation. Values are normalized with GAPDH of PAMs. Bars=mean±SD, n=3. *: p<0.05. n.s.: non-significant. FIG. 9D shows titration assay results for PRRSV in the culture media of PAMs treated as described in FIG. 9C. Bars=mean±SD, n=3, ***: p<0.001, n.s.: non-significant.

FIG. 10A shows daily body temperature (left y-axis) and body mass (g) (right y-axis) of control and B7-treated rat groups before (Day 0) and after treatment (Days 1-7). Mean±SD, n=4. FIG. 10B shows photographs of the gross anatomy of rats on Day 7 after blood withdrawal by heart ventricle puncture.

FIG. 11A shows neutrophils, hemoglobin, lymphocytes, and hematocrit levels for B7 versus the control. FIG. 11B shows ALP and AST concentrations for B7 versus the control. Data shown in Table 4.

DETAILED DESCRIPTION

Figure 1A:
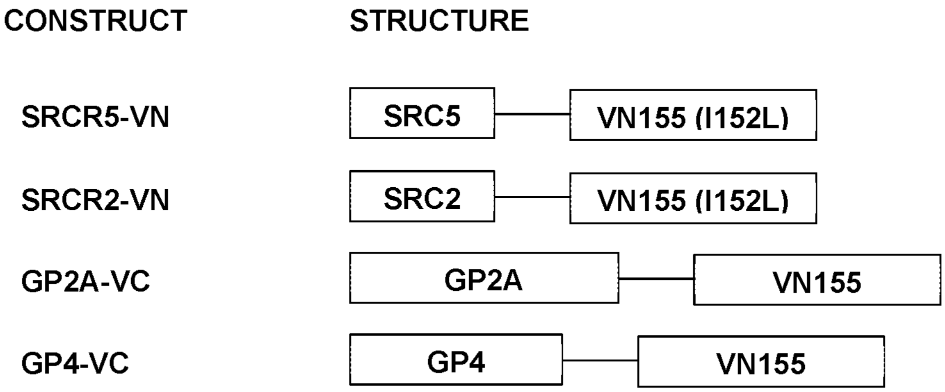
FIGS. 1A-E show BiFC assays and screening compounds that can inhibit the protein-protein interactions (PPI) between PRRSV and CD163.

Porcine reproductive and respiratory syndrome (PRRS) is one of the most economically devastating diseases affecting the pork industry globally. PRRS is caused by PRRS virus (PRRSV). Currently there are no effective treatments against this swine disease. Through artificial intelligence molecular screening, a set of small molecule compounds were obtained that were predicted to target the scavenger receptor cysteine-rich domain 5 (SRCR5) of CD163, which is a cell surface receptor specific for PRRSV infection. The inhibition of key PPIs between PRRSV and CD163 with natural or synthetic compounds is a unique approach against the PRRS panzootic, that can be utilized as an adjuvant to vaccination to diminish further viral loads and shedding. A cell-based bimolecular fluorescence complementation (BiFC) assay was developed to study the protein-protein interactions (PPI) between PRRSV glycoproteins and the CD163-SRCR5 domain. Using a BiFC assay, a list of small molecules predicted to bind the pig CD163-SRCR5 domain by artificial intelligence molecular screening using the AtomNet® model were screened to identify compounds that inhibit the protein-protein interactions between PRRSV glycoproteins and SRCR5. One compound was identified, with previously unverified function, 4-fluoro-2-methyl-N-[3-(3-morpholin-4-ylsulfonylanilino)quinoxalin-2-yl]benzenesulfonamide (designated here as B7), that significantly inhibits the interaction between the PRRSV glycoprotein (GP2a or GP4) and the CD163-SRCR5 domain. It was further demonstrated that compound B7 inhibits PRRSV infection of porcine alveolar macrophages (PAMs), the primary target of PRRSV in a dose-dependent manner. B7 significantly inhibited the infection caused by both type I and type II PRRSV strains. Further comparison and functional evaluation of chemical compounds structurally related to B7 revealed that the 3-(morpholinosulfonyl)aniline moiety of B7 or the 3-(piperidinylsulfonyl)aniline moiety in a B7 analogue is important for the inhibitory function against PRRSV infection. The present disclosure provides a novel strategy to potentially prevent PRRSV infection in pigs by blocking the PRRSV-CD163 interaction with small molecules.

Definitions

Unless otherwise defined, all technical and scientific terms used herein have the same meaning as commonly understood by one of ordinary skill in the art. For example, any nomenclatures used in connection with, and techniques of, cell and tissue culture, molecular biology, immunology, microbiology, genetics, and protein and nucleic acid chemistry and hybridization described herein are well known and commonly used in the art. In case of conflict, the present disclosure, including definitions, will control. Exemplary methods and materials are described below, although methods and materials similar or equivalent to those described herein can be used in practice or testing of the embodiments and aspects described herein.

As used herein, the terms "amino acid," "nucleotide," "polynucleotide," "vector," "polypeptide," and "protein" have their common meanings as would be understood by a biochemist of ordinary skill in the art. Standard single letter nucleotides (A, C, G, T, U) and standard single letter amino acids (A, C, D, E, F, G, H, I, K, L, M, N, P, Q, R, S, T, V, W, or Y) are used herein.

As used herein, the terms such as "include," "including," "contain," "containing," "having," and the like mean "comprising." The present disclosure also contemplates other embodiments "comprising," "consisting of," and "consisting essentially of," the embodiments or elements presented herein, whether explicitly set forth or not.

As used herein, the term "a," "an," "the" and similar terms used in the context of the disclosure (especially in the context of the claims) are to be construed to cover both the singular and plural unless otherwise indicated herein or clearly contradicted by the context. In addition, "a," "an," or "the" means "one or more" unless otherwise specified.

As used herein, the term "or" can be conjunctive or disjunctive.

As used herein, the term "substantially" means to a great or significant extent, but not completely.

As used herein, all percentages (%) refer to mass (or weight, w/w) percent unless noted otherwise.

As used herein, the term "about" or "approximately" as applied to one or more values of interest, refers to a value that is similar to a stated reference value, or within an acceptable error range for the particular value as determined by one of ordinary skill in the art, which will depend in part on how the value is measured or determined, such as the limitations of the measurement system. In one aspect, the term "about" refers to any values, including both integers and fractional components that are within a variation of up to ±10% of the value modified by the term "about." Alternatively, "about" can mean within 3 or more standard deviations, per the practice in the art. Alternatively, such as with respect to biological systems or processes, the term "about" can mean within an order of magnitude, in some embodiments within 5-fold, and in some embodiments within 2-fold, of a value. As used herein, the symbol "~" means "about" or "approximately."

All ranges disclosed herein include both end points as discrete values as well as all integers and fractions specified within the range. For example, a range of 0.1-2.0 includes 0.1, 0.2, 0.3, 0.4 . . . 2.0. If the end points are modified by the term "about," the range specified is expanded by a variation of up to ±10% of any value within the range or within 3 or more standard deviations, including the end points.

As used herein, the terms "active ingredient" or "active pharmaceutical ingredient" refer to a pharmaceutical agent, active ingredient, compound, or substance, compositions, or mixtures thereof, that provide a pharmacological, often beneficial, effect.

As used herein, the terms "control," or "reference" are used herein interchangeably. A "reference" or "control" level may be a predetermined value or range, which is employed as a baseline or benchmark against which to assess a measured result. "Control" also refers to control experiments or control cells.

As used herein, the term "dose" denotes any form of an active ingredient formulation or composition, including cells, that contains an amount sufficient to initiate or produce a therapeutic effect with at least one or more administrations. "Formulation" and "composition" are used interchangeably herein.

As used herein, the term "prophylaxis" refers to preventing or reducing the progression of a disorder, either to a statistically significant degree or to a degree detectable by a person of ordinary skill in the art.

As used herein, the phrases "effective amount" or "a therapeutically effective amount" of a compound described herein refers to an amount of the compound described herein that will elicit the biological or medical response of a subject, for example, reduction or inhibition of an enzyme or a protein activity, or ameliorate symptoms, alleviate conditions, slow or delay disease progression, or prevent a disease, etc. The result can be the reduction or alleviation of the signs, symptoms, or causes of a disease, or any other desired alteration of a biological system. An effective amount may be based on factors individual to each subject, including, but not limited to, the subject's age, size, type or extent of disease, stage of the disease, route of administration, the type or extent of supplemental therapy used, ongoing disease process, and type of treatment desired.

In one embodiment, the term "a therapeutically effective amount" refers to the amount of the compound described herein that, when administered to a subject, is effective to at least partially alleviate, prevent and/or ameliorate a condition, or a disorder or viral infections, respiratory conditions, reproductive conditions, congenital respiratory impairments, fevers, lethargy, loss of appetite, stillbirths, premature births, abortions, postweaning respiratory diseases, respiratory distress, depression, cyanosis of the ears, abdomen and vulva, or vomiting. In one embodiment, the term "a therapeutically effective amount" refers to the amount of the compound described herein that, when administered to a cell, or a tissue, or a non-cellular biological material, or a medium, is effective to treat or ameliorate viral infections, cell or tissue death, or protein-protein interactions.

As used herein, the term "subject" refers to an animal. Typically, the subject is a mammal. A subject also refers to primates (e.g., humans, male or female; infant, adolescent, or adult), non-human primates, rats, mice, rabbits, pigs, cows, sheep, goats, horses, dogs, cats, fish, birds, and the like. In one embodiment, the subject is a primate. In one embodiment, the subject is a human. In one embodiment, the subject is a pig.

As used herein, a subject is "in need of treatment" if such subject would benefit biologically, medically, or in quality of life from such treatment. A subject in need of treatment does not necessarily present symptoms, particular in the case of preventative or prophylaxis treatments.

As used herein, the terms "inhibit," "inhibition," or "inhibiting" refer to the reduction or suppression of a given biological process, condition, symptom, disorder, or disease, or a significant decrease in the baseline activity of a biological activity or process.

As used herein, "treatment" or "treating" refers to prophylaxis of, preventing, suppressing, repressing, reversing, alleviating, ameliorating, or inhibiting the progress of biological process including a disorder or disease, or completely eliminating a disease. A treatment may be either performed in an acute or chronic way. The term "treatment" also refers to reducing the severity of a disease or symptoms associated with such disease prior to affliction with the disease. "Repressing" or "ameliorating" a disease, disorder, or the symptoms thereof involves administering a cell, composition, or compound described herein to a subject after clinical appearance of such disease, disorder, or its symptoms. "Prophylaxis of" or "preventing" a disease, disorder, or the symptoms thereof involves administering a cell, composition, or compound described herein to a subject prior to onset of the disease, disorder, or the symptoms thereof. "Suppressing" a disease or disorder involves administering a cell, composition, or compound described herein to a subject after induction of the disease or disorder thereof but before its clinical appearance or symptoms thereof have manifest.

As used herein, "formulation" and "composition" can be used interchangeably and refer to a combination of at least two ingredients. In some embodiments, at least one ingredient may be an active agent or otherwise have properties that exert physiologic activity when administered to a subject As used herein, "therapeutic composition" and "pharmaceutical composition" can be used interchangeably and refer to a combination of at least two ingredients.

Definitions of specific functional groups and chemical terms are described in more detail herein. The chemical elements are identified in accordance with the Periodic Table of the Elements, CAS version, *Handbook of Chemistry and Physics,* 75$^{th}$ ed., inside cover, and specific functional groups are generally defined as described therein. Additionally, general principles of organic chemistry, as well as specific functional moieties and reactivity, are described in Thomas Sorrell, Organic Chemistry, University Science Books, Sausalito, 1999; Smith and March, *March's Advanced Organic Chemistry,* 5$^{th}$ ed, John Wiley & Sons, Inc., New York, 2001; Larock, *Comprehensive Organic Transformations*, VCH Publishers, Inc., New York, 1989; and Carruthers, *Some Modern Methods of Organic Synthesis,* 3$^{rd}$ ed, Cambridge University Press, Cambridge, 1987.

As used herein, the term "alkyl" refers to a radical of a straight chain or branched saturated hydrocarbon group having from 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, isobutyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl).

As used herein, the term "alkylene" refers to a divalent radical of an alkyl group, e.g., $—CH_2—$, $—CH_2CH_2—$, and $—CH_2CH_2CH_2—$.

As used herein, the term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and one or more heteroatoms within the parent chain ("hetero$C_{1-8}$ alkyl"). In some embodiments, a heteroalkyl group is a saturated group having 1 to 7 carbon atoms and one or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

As used herein, the term "heteroalkylene" refers to a divalent radical of a heteroalkyl group.

As used herein, the terms "alkoxy" or "alkoxyl" refers to an —O-alkyl radical. In some embodiments, the alkoxy groups are methoxy, ethoxy, n-propoxy, isopropoxy, n-butoxy, tert-butoxy, sec-butoxy, n-pentoxy, n-hexoxy, and 1,2-dimethylbutoxy. In some embodiments, alkoxy groups are lower alkoxy, i.e., with between 1 and 6 carbon atoms. In some embodiments, alkoxy groups have between 1 and 4 carbon atoms.

As used herein, the term "aryl" refers to a stable, aromatic, mono- or bicyclic ring radical having the specified number of ring carbon atoms. Examples of aryl groups include, but are not limited to, phenyl, 1-naphthyl, 2-naphthyl, and the like. The related term "aryl ring" likewise refers to a stable, aromatic, mono- or bicyclic ring having the specified number of ring carbon atoms.

As used herein, the term "heteroaryl" refers to a stable, aromatic, mono- or bicyclic ring radical having the specified number of ring atoms and comprising one or more heteroatoms individually selected from nitrogen, oxygen, or sulfur. The heteroaryl radical may be bonded via a carbon atom or heteroatom. Examples of heteroaryl groups include, but are not limited to, furyl, pyrrolyl, thienyl, pyrazolyl, imidazolyl, thiazolyl, isothiazolyl, oxazolyl, isoxazolyl, triazolyl, tetrazolyl, pyrazinyl, pyridazinyl, pyrimidyl, pyridyl, quinolinyl, isoquinolinyl, indolyl, indazolyl, oxadiazolyl, benzothiazolyl, quinoxalinyl, and the like. The related term "heteroaryl ring" likewise refers to a stable, aromatic, mono- or bicyclic ring having the specified number of ring atoms and comprising one or more heteroatoms individually selected from nitrogen, oxygen, or sulfur.

As used herein, the term "carbocyclyl" refers to a stable, saturated, or unsaturated, non-aromatic, mono- or bicyclic (fused, bridged, or spiro) ring radical having the specified number of ring carbon atoms. Examples of carbocyclyl groups include, but are not limited to, the cycloalkyl groups identified above, cyclobutenyl, cyclopentenyl, cyclohexenyl, and the like. In an embodiment, the specified number is $C_3$-$C_{12}$ carbons. The related term "carbocyclic ring" likewise refers to a stable, saturated, or unsaturated, non-aromatic, mono- or bicyclic (fused, bridged, or spiro) ring having the specified number of ring carbon atoms.

As used herein, the term "heterocyclyl" refers to a stable, saturated or unsaturated, non-aromatic, mono- or bicyclic (fused, bridged, or spiro) ring radical having the specified number of ring atoms and comprising one or more heteroatoms individually selected from nitrogen, oxygen and sulfur. The heterocyclyl radical may be bonded via a carbon atom or heteroatom. In an embodiment, the specified number is $C_3$-$C_{12}$ carbons. Examples of heterocyclyl groups include, but are not limited to, azetidinyl, oxetanyl, pyrrolinyl, pyrrolidinyl, tetrahydrofuryl, tetrahydrothienyl, piperidyl, piperazinyl, tetrahydropyranyl, morpholinyl, perhydroazepinyl, tetrahydropyridinyl, tetrahydroazepinyl, octahydropyrrolopyrrolyl, and the like. The related term "heterocyclic ring" likewise refers to a stable, saturated or unsaturated, non-aromatic, mono- or bicyclic (fused, bridged, or spiro) ring having the specified number of ring atoms and comprising one or more heteroatoms individually selected from nitrogen, oxygen and sulfur.

As used herein the terms "halo" or "halogen" refers to fluorine (fluoro, —F), chlorine (chloro, —Cl), bromine (bromo, —Br), or iodine (iodo, —I).

As used herein the term "substituted," whether preceded by the term "optionally" or not, means that one or more hydrogens of the designated moiety are replaced with a suitable substituent.

As used herein, the definition of each expression, e.g., alkyl, m, n, etc., when it occurs more than once in any structure, is intended to be independent of its definition elsewhere in the same structure.

Pharmaceutical Compositions

Disclosed herein are pharmaceutical compositions comprising:

an effective amount of compound of Formula I:

(I)

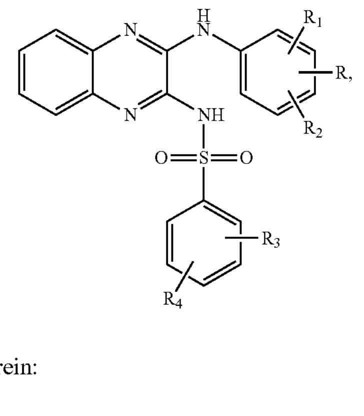

wherein:

R is

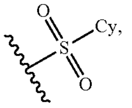

where Cy is 5- to 6-membered heterocyclylene or $C_{3-6}$ cycloalkylene, wherein Cy is unsubstituted or substituted with 1-6 substituents independently selected from $C_{1-4}$ alkyl, $C_{1-2}$ fluoroalkyl, or halogen;

$R^1$ and $R^2$ are each independently hydrogen, $C_{1-4}$ alkyl, $C_{1-2}$ fluoroalkyl, cyano, or halogen;

$R^3$ and $R^4$ are each independently hydrogen, $C_{1-4}$ alkyl, $C_{1-2}$ fluoroalkyl, cyano, or halogen;

with the proviso that:

when $R^3$ and $R^4$ are each hydrogen at least one of $R^1$ and $R^2$ is not hydrogen, where when one of $R^1$ or $R^2$ is hydrogen $R^2$ or $R^1$ is not chloro;

when $R^3$ or $R^4$ is methyl in the para-position R is not

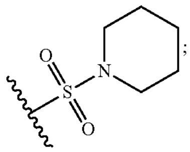 [SMILES: *S(=O)(=O)N1CCCCC1]

and when $R^3$ or $R^4$ is chloro in the para-position R is not

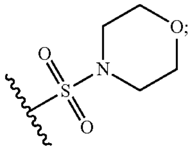 [SMILES: *S(=O)(=O)N1CCOCC1]

and one or more pharmaceutically acceptable excipients.

In some embodiments, R is

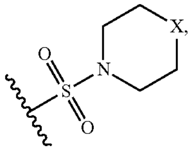

where X is O, NH, or $CH_2$.

In some embodiments, R is

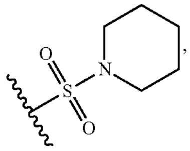

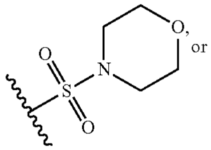

or

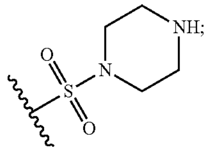

$R^1$ is hydrogen; and $R^2$, $R^3$, and $R^4$ are each independently hydrogen, methyl, or halogen.

In some embodiments, R is

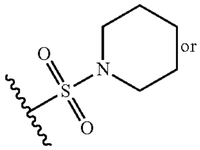

or

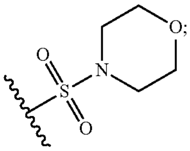

$R^1$ is hydrogen;

$R^2$ is hydrogen or halogen; and $R^3$ and $R^4$ are each independently hydrogen, methyl, or halogen.

In some embodiments, R is

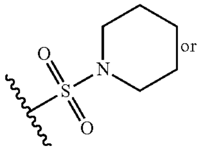

or

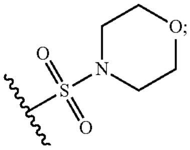

$R^1$ is hydrogen;

$R^2$ is halogen; and $R^3$ and $R^4$ are each independently hydrogen, methyl, or halogen.

In some embodiments, the compound is one of Formula II, or III:

(II)

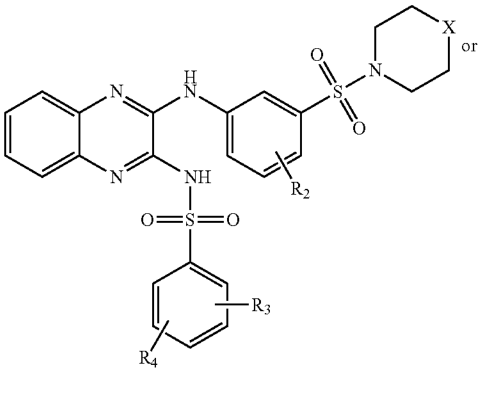

or

-continued (III)

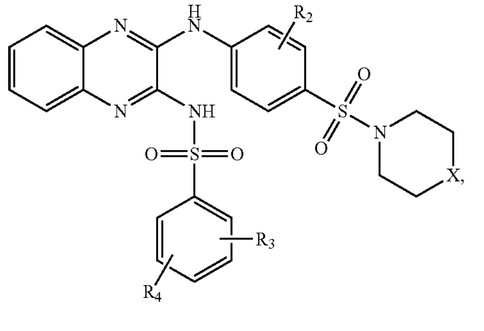

wherein:

X is O, NH, or $CH_2$; and $R^2$, $R^3$, and $R^4$ are each independently hydrogen, methyl, or halogen. In some embodiments, X is O. In some embodiments, X is $CH_2$. In some embodiments, X is NH. In some embodiments, $R^2$ is halogen or hydrogen. In some embodiments, $R^2$ is chloro. In some embodiments, $R^2$ is hydrogen. In some embodiments, $R^3$ is hydrogen or methyl and $R^4$ is hydrogen or halogen. In another aspect, $R^3$ is methyl and $R^4$ is halogen. In some embodiments, $R^3$ is hydrogen and $R^4$ is methyl. In some embodiments, $R^3$ is methyl and $R^4$ is fluoro. In another aspect, $R^3$ and $R^4$ are hydrogen. In some embodiments, the compound is selected from:

(B7)

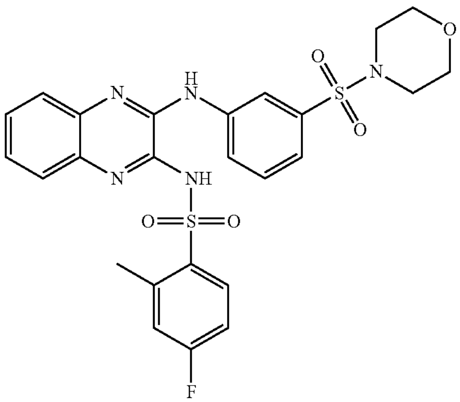

or (B7-A2)

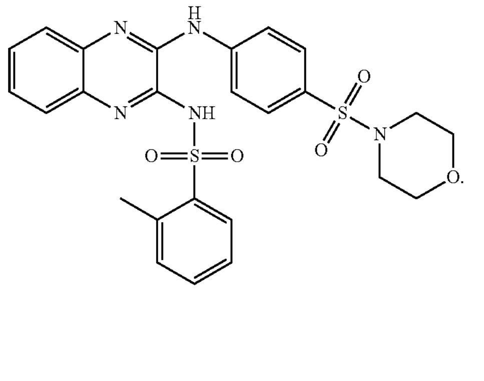

Also disclosed herein are pharmaceutical compositions comprising:

an effective amount of:

(B7)

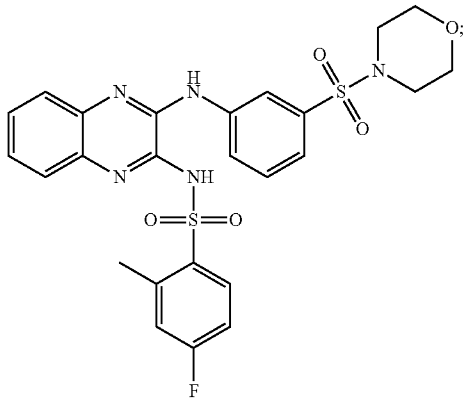

and one or more pharmaceutically acceptable excipients.

In some embodiments, the pharmaceutically acceptable excipients comprise buffering agents, solubilizers, solvents, antimicrobial preservatives, antioxidants, suspension agents, a tablet or capsule diluent, or a tablet disintegrant. In some embodiments, the compound of Formula I inhibits an interaction between scavenger receptor cysteine-rich domain 5 (SRCR5) of Cluster of Differentiation 163 (CD163) and glycoproteins of an arterivirus. In some embodiments, the compound of Formula I treats, ameliorates the symptoms of, or is prophylactic for an infection by an arterivirus. In some embodiments, the composition comprises about 5 mg to about 400 mg of the compound of Formula I.

Also disclosed herein is a pharmaceutical dosage form comprising a therapeutically effective amount of the pharmaceutical composition described herein.

In some embodiments, the therapeutically effective amount of the pharmaceutical composition comprises about 0.5 mg/kg to about 2.5 mg/kg of the compound of Formula I.

Also disclosed herein are uses of a pharmaceutical composition described herein for treating a reproductive respiratory syndrome by administering to a subject in need thereof an effective amount of the compound of Formula I.

Also disclosed herein are kits comprising one or more dosage forms of the pharmaceutical composition described herein. In some embodiments, the kit further comprises one or more packages, receptacles, delivery devices, labels, and/or instructions for use.

Pharmaceutical Compositions

The disclosed compositions can be incorporated into pharmaceutical compositions suitable for administration to a subject (such as a patient, which may be a human or non-human). The pharmaceutical composition can be prepared for administration to a subject. Such pharmaceutical compositions can be administered in dosages and by techniques well known to those skilled in the medical, veterinary, and pharmaceutical arts taking into consideration such factors as the age, sex, weight, and condition of the particular subject, and the route of administration.

The pharmaceutical compositions and formulations can include pharmaceutically acceptable carriers. The term "pharmaceutically acceptable carrier," as used herein, means a non-toxic, inert solid, semi-solid or liquid filler, diluent, encapsulating material, or formulation auxiliary of any type. Exemplary materials that can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, the compounds and their pharmaceutically acceptable salts can be formulated for administration by, for example, injection, inhalation (either through the mouth or the nose), solid dosing, eye drop, in a topical oil-based formulation, implants, oral, buccal, parenteral, or rectal administration. Techniques and formulations generally may be found in "*Remington's Pharmaceutical Sciences*," (Meade Publishing Co., Easton, Pa.). Therapeutic compositions must typically be sterile and stable under the conditions of manufacture and storage.

The route by which the disclosed compounds are administered, and the form of the composition, will dictate the type of carrier to be used. The composition can be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50% to about 90%.

Suitable lubricants include, but are not limited to, silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of lubricant(s) in a systemic or topical composition typically is about 5% to about 10%.

Suitable binders include, but are not limited to, polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition typically is about 5% to about 50%.

Suitable disintegrants include, but are not limited to, agar, alginic acid and the sodium salt thereof, effervescent mixtures, croscarmellose, crospovidone, sodium carboxymethyl starch, sodium starch glycolate, clays, and ion exchange resins. The amount of disintegrant(s) in a systemic or topical composition typically is about 0.1% to about 10%.

Suitable colorants include, but are not limited to, a colorant such as an FD&C dye. When used, the amount of colorant in a systemic or topical composition typically is about 0.005% to about 0.1%.

Suitable flavors include, but are not limited to, menthol, peppermint, and fruit flavors. The amount of flavor(s), when used, in a systemic or topical composition typically is about 0.1% to about 1.0%.

Suitable sweeteners include, but are not limited to, aspartame and saccharin. The amount of sweetener(s) in a systemic or topical composition typically is about 0.001% to about 1%.

Suitable antioxidants include, but are not limited to, butylated hydroxyanisole ("BHA"), butylated hydroxytoluene ("BHT"), and vitamin E. The amount of antioxidant(s) in a systemic or topical composition typically is about 0.1% to about 5%.

Suitable preservatives include, but are not limited to, benzalkonium chloride, methyl paraben and sodium benzoate. The amount of preservative(s) in a systemic or topical composition typically is about 0.01% to about 5%.

Suitable glidants include, but are not limited to, silicon dioxide. The amount of glidant(s) in a systemic or topical composition typically is about 1% to about 5%.

Suitable solvents include, but are not limited to, water, isotonic saline, ethyl oleate, glycerin, hydroxylated castor oils, alcohols such as ethanol, and phosphate buffer solutions. The amount of solvent(s) in a systemic or topical composition typically is from about 0% to about 100%.

Suitable suspending agents include, but are not limited to, AVICEL RC-591 (from FMC Corporation of Philadelphia, PA) and sodium alginate. The amount of suspending agent (s) in a systemic or topical composition typically is about 1% to about 8%.

Suitable surfactants include, but are not limited to, lecithin, Polysorbate 80, and sodium lauryl sulfate, and the TWEEN® detergents. Suitable surfactants include, but are not limited to, those disclosed in the C.T.F.A. Cosmetic Ingredient Handbook, 1992, pp. 587-592*; Remington's Pharmaceutical Sciences,* 15th Ed. 1975, pp. 335-337; and McCutcheon's Volume 1*, Emulsifiers & Detergents,* 1994, North American Edition, pp. 236-239. The amount of surfactant(s) in the systemic or topical composition typically is about 0.1% to about 5%.

Although the amounts of components in the systemic compositions may vary depending on the type of systemic composition prepared, in general, systemic compositions include about 0.01% to about 50% of an active compound and about 50% to about 99.99% of one or more carriers. Compositions for parenteral administration typically include about 0.1% to about 10% of an active compound and about 90% to about 99.9% of a carrier including a diluent and a solvent.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a disclosed compound and a carrier, namely, a carrier selected from diluents, colorants, flavors, sweeteners, preservatives, solvents, suspending agents, and surfactants. In some embodiments, peroral liquid compositions include one or more ingredients selected from colorants, flavors, and sweeteners.

Other compositions useful for attaining systemic delivery of the subject compounds include sublingual, buccal and nasal dosage forms. Such compositions typically include one or more of soluble filler substances such as diluents including sucrose, sorbitol, and mannitol; and binders such as acacia, microcrystalline cellulose, carboxymethyl cellulose, and hydroxypropyl methylcellulose. Such compositions can further include lubricants, colorants, flavors, sweeteners, antioxidants, and/or glidants.

The amount of the carrier employed in conjunction with a disclosed compound is sufficient to provide a practical quantity of composition for administration per unit dose of the compound. Techniques and compositions for making dosage forms useful in the methods of this invention are described in the following references: *Modern Pharmaceutics*, Chapters 9 and 10, Banker & Rhodes, eds. (1979); Lieberman et al., *Pharmaceutical Dosage Forms: Tablets* (1981); and Ansel, *Introduction to Pharmaceutical Dosage Forms,* 2nd Ed., (1976).

Pharmaceutical excipients useful for the compositions as described herein include, but are not limited to: acidifying agents (acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid); alkalizing agents (ammonia solution, ammonium carbonate, diethanolamine, diisopropanolamine, potassium hydroxide, sodium bicarbonate, sodium borate, sodium carbonate, sodium hydroxide, trolamine); antifoaming agents (dimethicone, simethicone); antimicrobial preservatives (benzalkonium chloride, benzalkonium chloride solution, benzethonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, ascorbic acid, thimerosal, thymol); antioxidants (ascorbic acid, ascorbyl palmitate, butylated hydroxyanisole, butylated hydroxytoluene, hypophosphorous acid, monothioglycerol, propyl gallate, sodium formaldehyde sulfoxylate, sodium metabisulfite, sodium thiosulfate, sulfur dioxide, tocopherol, tocopherols excipient); buffering agents (acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate); chelating agents (edetate disodium, ethylenediaminetetraacetic acid and salts, edetic acid); coating agents (sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyvinyl acetate phthalate, shellac, sucrose, titanium dioxide, carnauba wax, microcrystalline wax, zein); colorants (caramel, red, yellow, black or blends, ferric oxide); complexing agents (ethylenediaminetetraacetic acid and salts (EDTA), edetic acid, gentisic acid ethanolamide, oxyquinoline sulfate); desiccants (calcium chloride, calcium sulfate, silicon dioxide); emulsifying and/or solubilizing agents (acacia, cholesterol, diethanolamine (adjunct), glyceryl monostearate, lanolin alcohols, mono- and di-glycerides, monoethanolamine (adjunct), lecithin, oleic acid (adjunct), oleyl alcohol (stabilizer), poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, diacetate, monostearate, sodium lauryl sulfate, sodium stearate, sorbitan monolaurate, sorbitan monooleate, sorbitan monopalmitate, sorbitan monostearate, stearic acid, trolamine, emulsifying wax); filtering aids (powdered cellulose, purified siliceous earth); flavors and perfumes (anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin); humectants (glycerol, hexylene glycol, sorbitol); plasticizers (e.g., castor oil, diacetylated monoglycerides, diethyl phthalate, glycerol, mono- and di-acetylated monoglycerides, propylene glycol, triacetin, triethyl citrate); polymers (e.g., cellulose acetate, alkyl celluloses, hydroxyalkyl, acrylic polymers and copolymers); solvents (acetone, alcohol, diluted alcohol, amylene hydrate, benzyl benzoate, butyl alcohol, carbon tetrachloride, chloroform, corn oil, cottonseed oil, ethyl acetate, glycerol, hexylene glycol, isopropyl alcohol, methyl alcohol, methylene chloride, methyl isobutyl ketone, mineral oil, peanut oil, propylene carbonate, sesame oil, water for injection, sterile water for injection, sterile water for irrigation, purified water); sorbents (powdered cellulose, charcoal, purified siliceous earth); carbon dioxide sorbents (barium hydroxide lime, soda lime); stiffening agents (hydrogenated castor oil, cetostearyl alcohol, cetyl alcohol, cetyl esters wax, hard fat, paraffin, polyethylene excipient, stearyl alcohol, emulsifying wax, white wax, yellow wax); suspending and/or viscosity-increasing agents (acacia, agar, alginic acid, aluminum monostearate, bentonite, purified bentonite, magma bentonite, carbomer, carboxymethylcellulose calcium, carboxymethylcellulose sodium, carboxymethylcellulose sodium carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, alginate, silicon dioxide, colloidal silicon dioxide, sodium alginate, tragacanth, xanthan gum); sweetening agents (aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup); surfactants (simethicone); tablet binders (acacia, alginic acid, sodium carboxymethylcellulose, microcrystalline cellulose, dextrin, ethylcellulose, gelatin, liquid glucose, guar gum, hydroxypropyl methylcellulose, methylcellulose, polyethylene oxide, povidone, pregelatinized starch, syrup); tablet and/or capsule diluents (calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar); tablet disintegrants (alginic acid, microcrystalline cellulose, croscarmellose sodium, crospovidone, polacrilin potassium, sodium starch glycolate, starch, pregelatinized starch); tablet and/or capsule lubricants (calcium stearate, glyceryl behenate, magnesium stearate, light mineral oil, sodium stearyl fumarate, stearic acid, purified stearic acid, talc, hydrogenated vegetable oil, zinc stearate); thickening agents (gelatin having a bloom strength of 50-100); tonicity agent (dextrose, glycerol, mannitol, potassium chloride, sodium chloride); vehicle: flavored and/or sweetened (aromatic elixir, compound benzaldehyde elixir, iso-alcoholic elixir, peppermint water, sorbitol solution, syrup, tolu balsam syrup); vehicle: oleaginous (almond oil, corn oil, cottonseed oil, ethyl oleate, isopropyl myristate, isopropyl palmitate, mineral oil, light mineral oil, myristyl alcohol, octyl dodecanol, olive oil, peanut oil, persic oil, sesame oil, soybean oil, squalane); vehicle: solid carrier (sugar spheres); vehicle: sterile (bacteriostatic water for injection, bacteriostatic sodium chloride injection); viscosity-increasing (see suspending agent); water repelling agents (cyclomethicone, dimethicone, simethicone); and/or solubilizing agent (benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaurate, sorbitan monooleate, sorbitan monopalmitate, sorbitan monostearate, tyloxapol). This list is not meant to be exclusive, but instead merely representative of the classes of excipients and the particular excipients that may be used in oral dosage forms as described herein. See *Remington's Essentials of Pharmaceutics*, Pharmaceutical Press Publishing Company, London, UK, 1$^{st}$ Edition, 2013, and the *Handbook of Pharmaceutical Excipients,* 8$^{th}$ Edition, Pharmaceutical Press Publishing Company London, U K, 2017, each of which is incorporated by reference herein for such teachings.

Also described herein are methods for manufacturing a dosage form comprising formulating a composition as described herein comprising sprays, capsules, tablets, elixirs, emulsions, lozenges, suspensions, syrups, pills, lotions, epidermal patches, suppositories, inhalers, or injectables. Any methods known to the art for formulating extracts or active principal ingredients into lotions, soaps, etc. can be utilized.

Pharmaceutically Acceptable Salts

The disclosed compounds can exist as a pharmaceutically acceptable salt. The term "pharmaceutically acceptable salt" refers to salts or zwitterions of the compounds that are water or oil-soluble or dispersible, suitable for treatment of disorders without undue toxicity, irritation, and allergic response, commensurate with a reasonable benefit/risk ratio and effective for their intended use. The salts can be prepared during the final isolation and purification of the compound or separately by reacting an amino group of the compound with a suitable acid. For example, a compound can be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric and the like. The amino groups of the compound may also be quaternized with alkyl chlorides, bromides, and iodides such as methyl, ethyl, propyl, isopropyl, butyl, lauryl, myristyl, stearyl and the like.

Basic addition salts may be prepared during the final isolation and purification of the disclosed compound by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, N,N'-dibenzylethylenediamine, ethylenediamine, ethanolamine, diethanolamine, piperidine, piperazine, and the like.

Methods of Treatment

In some embodiments, the compounds and pharmaceutical compositions described herein are useful for treating the disorders described herein in a subject in need thereof.

As used herein, the terms "subject" and "patient" may be used interchangeably to refer to any vertebrate including, but not limited to, mammals and humans. In some embodiments, the subject may be a pig. In some embodiments, the subject is undergoing forms of treatment.

The terms "dosage" and "dose" are understood to mean an amount of an active agent that is suitable for administration to a subject in order achieve or otherwise contribute to a therapeutic effect. In some examples, a dosage unit refers to a single dose that is administered to a subject, and is readily handled and packed, remaining as a physically and chemically stable unit dose.

Administration

The pharmaceutical compositions and formulations may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition often is determined by a person skilled in the art and may vary according to factors such as the disease state, age, sex, and weight of the individual, and the ability of the composition to elicit a desired response in the individual. A therapeutically effective amount is also one in which any toxic or detrimental effects of a compound of the invention are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of an active compound may be in the range of 1 mg to about 1000 mg of one or more of the compounds described herein. In one aspect, the therapeutically effective amount is about 5 mg to about 400 mg, including all integers and fractions within the range. In another aspect, the therapeutically effective amount is about: 2.5 mg, 5 mg, 10 mg, 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, 400 mg, 410 mg, 420 mg, 430 mg, 440 mg, 450 mg, 460 mg, 470 mg, 480 mg, 490 mg, or 500 mg of one or more of the compounds described herein.

In another embodiment, the therapeutically effective amount of the compounds described herein is about: 0.1 mg/kg, 0.25 mg/kg, 0.5 mg/kg, 0.75 mg/kg, 1 mg/kg, 1.5 mg/kg, 2.0 mg/kg, 2.5 mg/kg, 3 mg/kg, 4 mg/kg, 5 mg/kg, 6 mg/kg, 7 mg/kg, 8 mg/kg, 9, mg/kg, or 10 mg/kg. In one aspect, the therapeutically effective amount is about 0.5 mg/kg to about 2.5 mg/kg including all integers and fractions within the range.

One or more dosage forms of the compositions described herein can be administered, for example, 1×, 2×, 3×, 4×, 5×, 6×, or even more times per day. One or more dosage forms can be administered, for example, for 1, 2, 3, 4, 5, 6, 7 days, or even longer. One or more dosage forms can be administered, for example, for 1, 2, 3, 4 weeks, or even longer. One or more dosage forms can be administered, for example, for 1, 2, 3, 4, 5, 6, 7, 8, 9, 10, 11, 12 months, 1 year, 2, years, 3 years, 4 years, 5 years, over 5 years, a decade, multiple decades, or even longer. One or more dosage forms can be administered at a regular interval until the subject or subject in need thereof, does not require treatment, prophylaxis, or amelioration of any disease or condition including but not limited to a viral infection or the symptoms thereof. In one aspect, the virus is an arterivirus. In another aspect, the subject is at risk of contracting, has contracted, or has symptoms associated with porcine reproductive and respiratory syndrome virus (PRRSV).

In one embodiment, the compositions described herein can be administered as dosage forms in various regimens, including one dose per day (QD), two doses per day (BID), three doses per day (TID), or four times per day (QID) to achieve a total daily dosage. In another embodiment, any of the foregoing doses comprise a total daily dosage.

Described herein are methods for treating a reproductive respiratory syndrome by administering to a subject in need thereof an effective amount of a compound of Formula I:

(I)

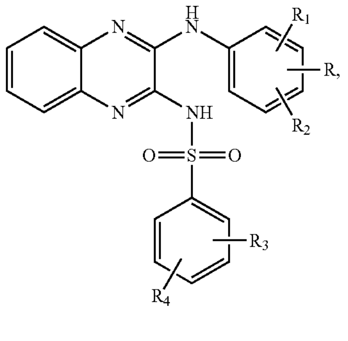

wherein:

R is

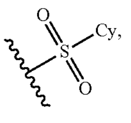

where Cy is 6- or 5-membered heterocyclylene or $C_{3-6}$ cycloalkylene, wherein Cy is unsubstituted or substituted with 1-6 substituents independently selected from $C_{1-4}$ alkyl, $C_{1-2}$ fluoroalkyl, or halogen;

$R^1$ and $R^2$ are each independently hydrogen, $C_{1-4}$ alkyl, $C_{1-2}$ fluoroalkyl, cyano, or halogen; and $R^3$ and $R^4$ are different or the same, wherein $R^3$ and $R^4$ are each independently $C_{1-4}$ alkyl, halogen, hydrogen, $C_{1-2}$ fluoroalkyl, or cyano.

In one aspect, R is

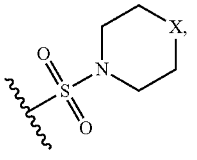

where X is O, NH, or $CH_2$. In some embodiments, the reproductive respiratory syndrome comprises one or more of the following symptoms: fever; lethargy; loss of appetite; vomiting; cough; sneezing; wheezing; labored breathing; high blood pressure; low blood pressure; respiratory distress; depression; cyanosis of the ears, abdomen, or vulva, stillbirths, premature births; abortions; postweaning respiratory diseases; pulmonary edema, or cardiac arrest. In some embodiments, decreased function of pulmonary alveolar and intravascular macrophages causes the reproductive respiratory syndrome. In some embodiments, the compound of Formula I is administered to the subject prior to, during, and after infection with an arterivirus. In some embodiments, the compound of Formula I is administered to the subject after infection with an arterivirus. In another aspect, the subject is a mammal. In some embodiments, the subject is a pig. In some embodiments, the administration is oral, nasal, topical, intravenous, subcutaneous, intramuscular, intravaginal, or intrarectal.

Also described herein are methods for inhibiting an interaction between scavenger receptor cysteine-rich domain 5 (SRCR5) of Cluster of Differentiation 163 (CD163) and glycoproteins of an arterivirus by administering to a subject in need thereof an effective amount of a compound of Formula I:

(I)

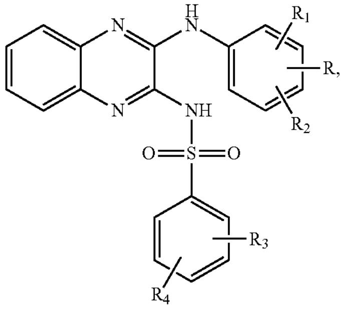

wherein:

R is

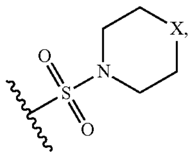

where X is O, NH, or $CH_2$; and $R^1$, $R^2$, $R^3$, and $R^4$ are each independently hydrogen, methyl, or halogen. In some embodiments, the arterivirus is porcine reproductive and respiratory syndrome virus (PRRSV). In some embodiments, the PRRSV is VR-2332, SDSU73, NADC30 (Type II), or Lelystad (Type I). In some embodiments, the glycoproteins comprise glycoprotein 2a precursor (GP2a) or glycoprotein 4 precursor (GP4). In some embodiments, the CD163 is expressed by monocytes or macrophages. In another aspect, the compound of Formula I treats, ameliorates the symptoms of, or is prophylactic for an infection of the subject by the arterivirus. In some embodiments, the subject is a pig. In another aspect, the arterivirus infects upper respiratory system, spleen, thymus, tonsils, lymph nodes, and Peyer's patches. In some embodiments, the compound of Formula I reduces viral titer by at least about 1.5 log.

Also disclosed herein are methods for treating, ameliorating the symptoms of, prophylaxis of, or lessening the viral burden of a pig infected with an arterivirus comprising administering a therapeutically effective amount of a pharmaceutical composition comprising one or more pharmaceutically acceptable excipients and one or more compounds selected from:

(B7)

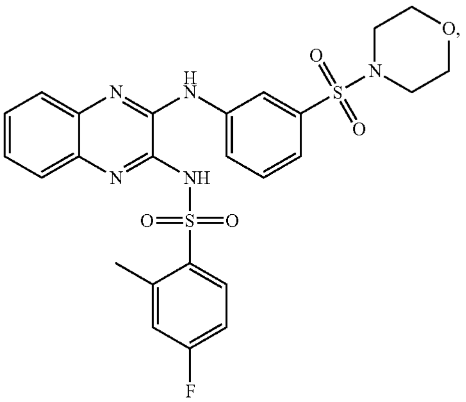

-continued (B7-A1)

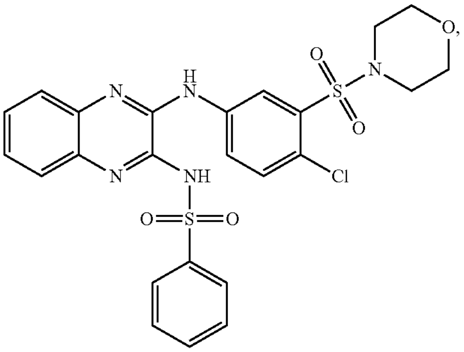

(B7-A2)

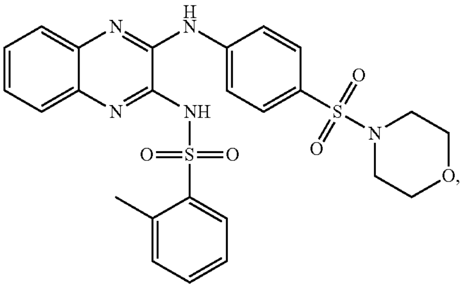

(B7-A3)

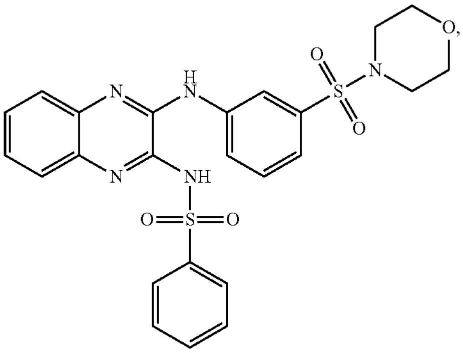

or (B7-A4)

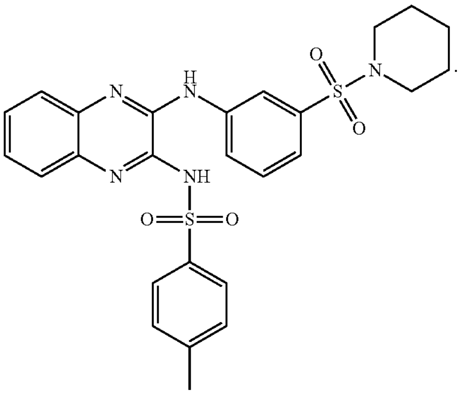

In some embodiments, the compound is:

(B7)

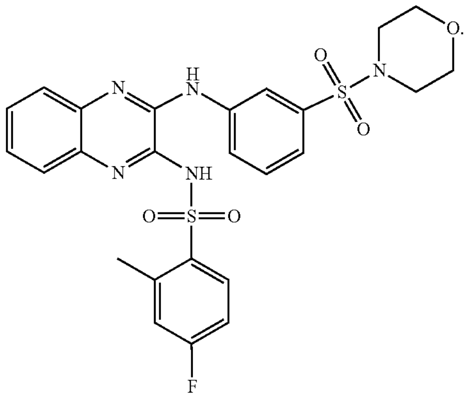

In some embodiments, one or more analgesics, anti-virals, anti-infectives, expectorants, decongestants, anti-fever, or other pharmaceutical agents are co-administered. In some embodiments, the therapeutically effective amount of the compounds is about 0.5 mg/kg to about 2.5 mg/kg.

Also disclosed herein is a pharmaceutical combination comprising one or more of the compounds described herein, and one or more additional therapeutic agent(s) for simultaneous, separate, or sequential use for treating or preventing a viral infection such as porcine reproductive and respiratory syndrome virus (PRRSV). In one embodiment, the additional therapeutic agent comprises one or more of analgesics, expectorants, decongestants, anti-fever, anti-viral agents, anti-fungal agents, anti-parasitic agents, antibiotics, immunomodulatory agents, anti-inflammatory agents, general anti-infective agents, vitamins, electrolytes, or food sources. In one aspect, one or more analgesics, anti-infectives, expectorants, decongestants, anti-fever, or other pharmaceutical agents are co-administered.

It will be apparent to one of ordinary skill in the relevant art that suitable modifications and adaptations to the compositions, formulations, methods, processes, and applications described herein can be made without departing from the scope of any embodiments or aspects thereof. The compositions and methods provided are exemplary and are not intended to limit the scope of any of the specified embodiments. All the various embodiments, aspects, and options disclosed herein can be combined in any variations or iterations. The scope of the compositions, formulations, methods, and processes described herein include all actual or potential combinations of embodiments, aspects, options, examples, and preferences herein described. The compositions, formulations, or methods described herein may omit any component or step, substitute any component or step disclosed herein, or include any component or step disclosed elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms or phrases in this disclosure are controlling. Furthermore, the specification discloses and describes merely exemplary embodiments. All patents and publications cited herein are incorporated by reference herein for the specific teachings thereof.

EXAMPLES

Example 1

Chemicals, Cells, and Viruses

All screening compounds were provided by Atomwise Inc. (CA, USA) as part of the Artificial Intelligence Molecular Screen (AIMS) awards program through Mcule, Inc. (CA, USA), or purchased directly from MolPort, Inc (NY, USA). PAMs were harvested from 6 healthy 4-6-month old and PRRSV-negative Landrace/Yorkshire cross pigs. Briefly, pigs were euthanized before slaughtering. Lungs were removed and transferred on ice to a cell culture cabinet. Warm PBS was injected with 200 U/mL penicillin and 200 μg/mL streptomycin through trachea bronchi into both sides of the lungs. The lungs were massaged and the bronchoalveolar lavage fluid (BALF) was removed. The BALF was centrifuged at 400×g for 15 min, the pellets contained pulmonary alveolar macrophages (PAMs). The pellets were then washed twice with warm complete medium. Cells were counted and frozen in 90% FBS (HI, Rocky Mountain Biologicals, Inc) and 10% DMSO (Sigma). Cells were stored in Mr. Frosty Freezing Container (Nalgene, USA), and incubated at −80° C. before being transferred to liquid nitrogen. PAMs were cultivated in RPMI-1640 (Gibco) supplemented with 10% FBS (HI, Rocky Mountain Biologicals, Inc), 2 mM Glutamax (Invitrogen), 0.1 mM MEM Non-Essential Amino Acids (Gibco), 1 mM sodium pyruvate (Gibco), 100 U/mL penicillin, 100 μg/mL streptomycin (Gibco), and 0.5 μg/mL Amphotericin B (Gibco). All PRRSV strains were propagated and titrated in MARC-145 cells.

Artificial Intelligence Molecular Screen (AIMS)

Virtual screening was performed using the AtomNet® model, the first deep neural network for structure-based drug design trained to predict protein-ligand binding affinity, Wallach et al., arxivorg 2015. For targeting the interaction between the porcine CD163 and PRRSV glycoprotein (GP2a or GP4), the X-ray structure of CD163-SRCR5 domain (PDB Accession Number: 5HRJ) was used to define a screening site centered around R561 comprising residues C502, S503, D505, W540, A541, E543, A559, P560, R561, P562, D563, G564, and C566. The Mcule library of commercially available organic small molecule compounds (~4 million v20171018) was prepared and screened, as described previously, using an ensemble of protein-ligand conformations. See Hsieh et al., *Cell Metab.* 30(6):1131-1140 (2019). Each of the 4 million molecules was scored and ranked by the AtomNet® model, following which a top set of 200 chemically diverse compounds was further inspected for undesirable substructures and molecular properties before 74 compounds were obtained for experimental testing.

Plasmid Construction

The N-terminus and C-terminus of the truncated Venus-I152L were inserted into vector backbone pMyc-CMV and pCMV-HA, constituting commercial plasmids pBiFC-VN155(I152L) and pBiFC-VC155, respectively (Addgene, Watertown, MA, USA). See Kodama and Hu, *Biotechniques* 49:793-805 (2010). cDNA fragments for the scavenger receptor cysteine-rich domain 2 (SRCR2) and SRCR5 of porcine CD163 receptor, and for PRRSV glycoproteins GP2a and GP4 were amplified by RT-PCR. The amplified cDNA fragments of SRCR2 or SRCR5 were subcloned into the pBiFC-VN155(I152L) vector digested with EcoRI/BglII. For constructions of GP2a and GP4 fusion proteins, cDNA fragments encoding GP2a or GP4 were subcloned into the pBiFC-VC155 vector digested with EcoRI/BglII. All plasmid clones were verified by DNA Sanger sequencing.

BiFC Assay

HEK293T cells cultured in 12-well plates were transfected with appropriate plasmids for each BiFC assay using FuGENE® 6 (Promega, Madison, WI, USA). After 5 h, various concentrations of chemical compounds were added to the culture media. DMSO was used as the vehicle control. Fluorescence images of treated cells at 24 h after plasmid transfection were captured using an inverted Nikon fluorescence microscope. Fluorescence intensity of treated cells was measured by ImageJ.

Cytotoxicity Assay

The cytotoxicity of selected screening compounds was determined in porcine alveolar macrophages (PAMs) the principal host cell of productive PRRSV infection. Briefly, various concentrations of the compounds were added to PAMs seeded in 24-well plates and incubated for 24 h. Then 50 μl of the MTT assay labeling reagent (In Vitro Toxicology Assay Kit, MTT based, Sigma-Aldrich) were added to each well and incubated for 4 h before 500 μl of the solubilization solution was added into each well to fully dissolve the formazan crystal by overnight incubation. The absorbance of samples was measured using a spectrophotometry microplate reader at 600 nm. PAMs treated with DMSO served as the controls.

Quantitative Reverse Transcription-PCR (qRT-PCR)

Total RNA was extracted from PAMs infected with PRRSV using RNeasy Mini Kit (Qiagen, Germantown, MD) according to the manufacturer's instruction. RNA concentrations were measured using a Nanodrop spectrophotometer (Thermo Fisher Scientific). Specific real time qPCR primers for the ORF7 gene of the four PRRSV strains and for porcine GAPDH are shown in Table 1. GAPDH was used as a housekeeping gene for gene expression normalization. Data were processed with the software associated with ABI 7500.

TABLE 1

Primers for qRT-PCR

| Name | Sequence (5'→3') | SEQ ID NO |
|---|---|---|
| Lelystad-Fwd | AAGATGACATCCGGCACCAC | SEQ ID NO: 1 |
| Lelystad-Rev | CCGGCAGCATAAACTCAACCTG | SEQ ID NO: 2 |
| VR2332-Fwd | AAACCAGTCCAGAGGCAAGG | SEQ ID NO: 3 |
| VR2332-Rev | GCAAACTAAACTCCACAGTGTAA | SEQ ID NO: 4 |
| SDSU73-Fwd | CCCTAGTGAGCGGCAATTGTGTC | SEQ ID NO: 5 |
| SDSU73-Rev | GGCGCACAGTATGATGCGTC | SEQ ID NO: 6 |
| NADC30-Fwd | GGATGGCCAGCCAGTCAATC | SEQ ID NO: 7 |
| NADC30-Rev | TGACGTCATCTTCAGTCGCTAGAG | SEQ ID NO: 8 |
| GAPDH-Fwd | CATCCTGGGCTACACTGAGG | SEQ ID NO: 9 |
| GAPDH-Rev | GCTTGACGAAGTGGTCGTTG | SEQ ID NO: 10 |

Western Blotting

Whole cell proteins were isolated from HEK293T cells. Briefly, the cells were rinsed twice with cold PBS. After removing the PBS, cold RIPA buffer (Thermo Fisher Scientific) supplemented with 1% (v/v) protease and phosphatase inhibitors was added to the cells and placed on ice for 5 min. Protein concentrations were determined using Pierce BCA Protein Assay Kit (Thermo Fisher Scientific). Equal amount of denatured proteins from each sample were separated on 10% SDS-PAGE and transferred onto a PVDF membrane. The membrane was incubated with 5% skim milk to block nonspecific binding before incubation with Myc-Tag mouse monoclonal antibody (1:1000, Cell Signaling Technology, Danvers, MA) or anti-GAPDH antibody (1:1,000; Cell Signaling Technology, Danvers, MA) overnight at 4° C. After washing with 1× T-BST, the membrane was incubated with HRP-conjugated secondary antibody (Cell Signaling Technology, Danvers, MA) for 1 h at room temperature, and image developed with ECL Blotting Substrates (Bio-Rad) and visualized under the ChemiDox XRS Image System (Bio-Rad).

PRRSV Infection and Titration Assay

For PRRSV infection of PAM cells, PAMs were seeded one day prior to infection. Control cells were treated with DMSO and test cells were treated with the selected screening compounds (5-20 μM) for 4 h before inoculation, during the 1 h PRRSV inoculation, and for 24 h after inoculation. Cells were inoculated with VR-2332, SDSU73, NADC30 or Lelystad PRRSV at MOI=0.1 for 1 h. The 24 h cell medium supernatant was stored at −80° C. until use.

For PRRSV titration assay, MARC145 cells were seeded in 48-well plates and grew to ~80% density before inoculation. Viral supernatants were prepared by 10-fold serial dilution, and 100 μl of the dilutions was added per well in six replicates. Inocula were removed from cells after 2 h and replaced with 0.5 mL of DMEM supplemented with 2% FBS, 2 mM glutamine, 0.1 mM MEM non-essential amino acids, 50 U/mL penicillin, and 50 μg/mL streptomycin (Invitrogen). Cells were cultured at 37° C. for 6 days and any cytopathic effects were observed and recorded. The PRRSV titer was calculated using the Reed and Muench method and expressed as median tissue culture infectious dose (TCID50/mL). Reed and Muench, *Am. J. Epidemiol.* 27(3): 493-497 (1938).

Statistical Analyses

All experiments were performed at least 3 times. Data were analyzed by one-way ANOVA with Tukey's post hoc comparison or by paired t-test. Data were expressed as mean±sd and $p<0.05$ was considered significant.

Example 2

Development of BiFC Assays to Identify Small Molecules that Inhibit the Protein-Protein Interactions Between PRRSV and CD163

Figure 1B:
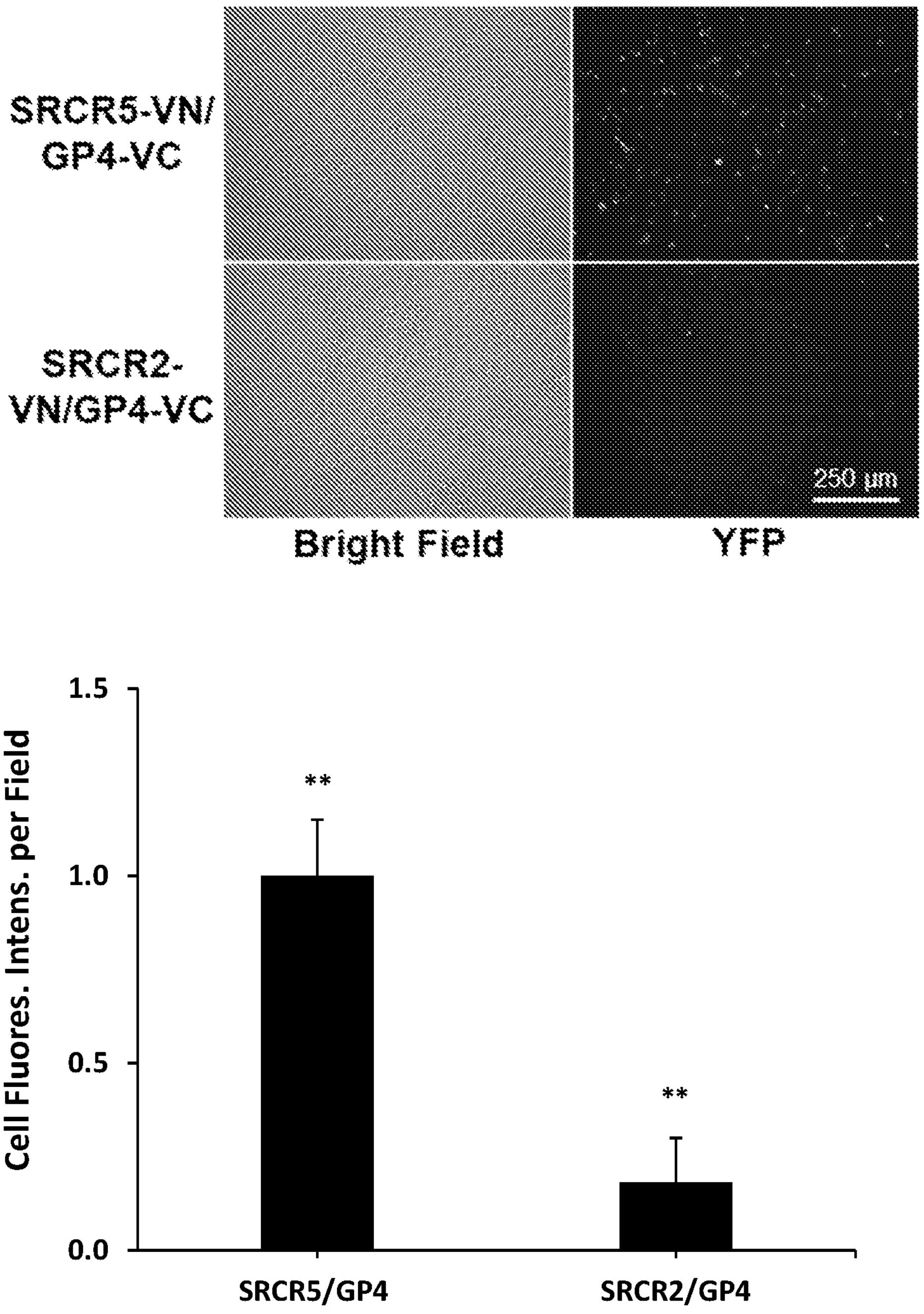
Figure 1C:
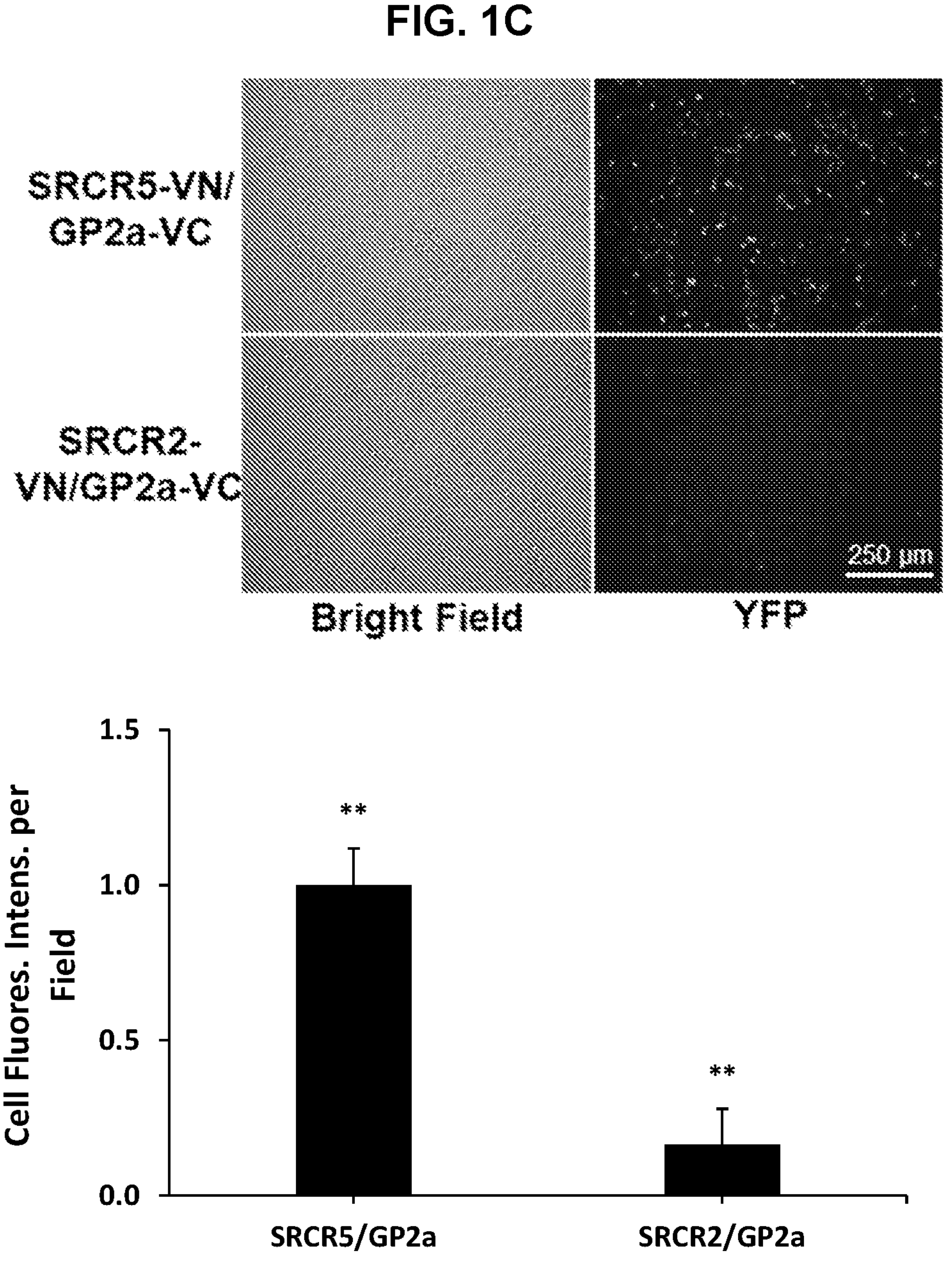
Figure 2:
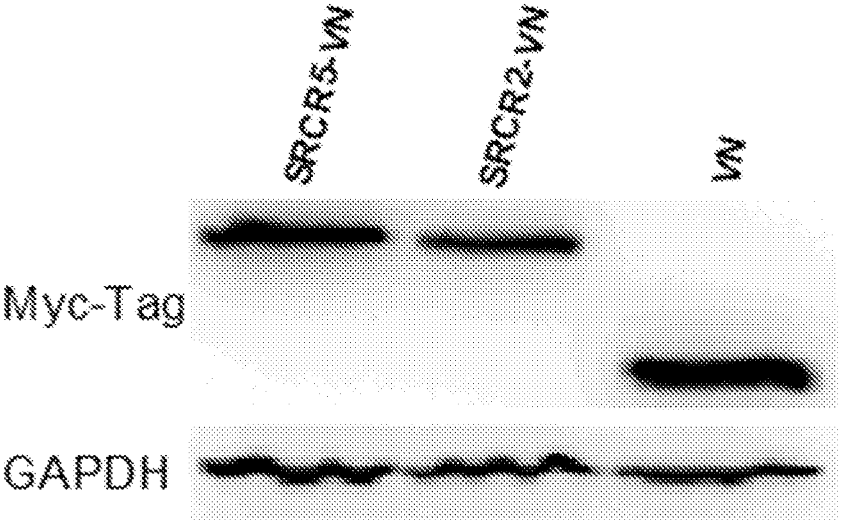
FIG. 2 shows a Western blot of the BiFC SRCR5-VN, SRCR2-VN, and vector VN proteins.

Using the previously described BiFC vector based on the fragmented venus protein (VN-155[I152L], hereafter named VN) and (VC-155, hereafter named VC), fusion protein constructs were established between the porcine CD163 protein SRCR5 or SRCR2 domain and VN, and between the PRRSV minor glycoproteins (GP2a or GP4) and VC (FIG. 1A, 2). See Kodama et al., *Biotechniques* 49(5): 793-805 (2010). These plasmids were co-expressed in HEK293T cells to evaluate the PPIs between the SRCR5 domain and GP2a or GP4. In agreement with the demonstrated critical role of CD163-SRCR5 in mediating the PRRSV/CD163 interaction and PRRSV infection, the CD163-SRCR5/VN fusion protein (SRCR5-VN) interacts with GP2a- or GP4-VC, with strong fluorescence detected under the microscope (FIG. 1B, 1C). In contrast, the fusion protein of CD163-SRCR2 domain (SRCR2-VN), which is dispensable for the PRRSV infection and PRRSV-CD163 interaction, only showed background fluorescence when co-expressed with GP2a- or GP4-VC (FIG. 1B, 1C). These data support that the porcine CD163-SRCR5 domain interacts directly with PRRSV glycoproteins GP2a and GP4.

Figure 1D:
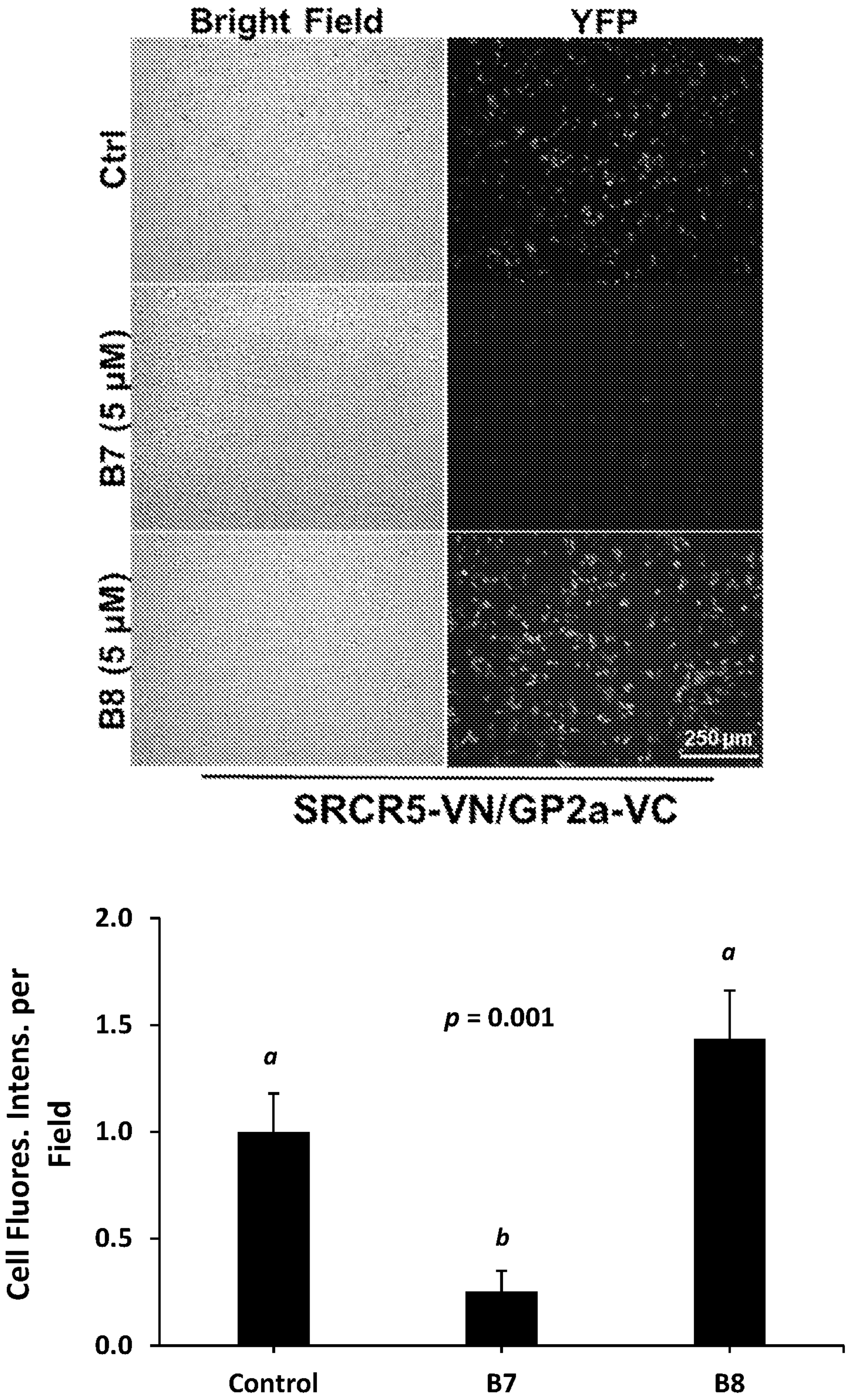
Figure 1E:
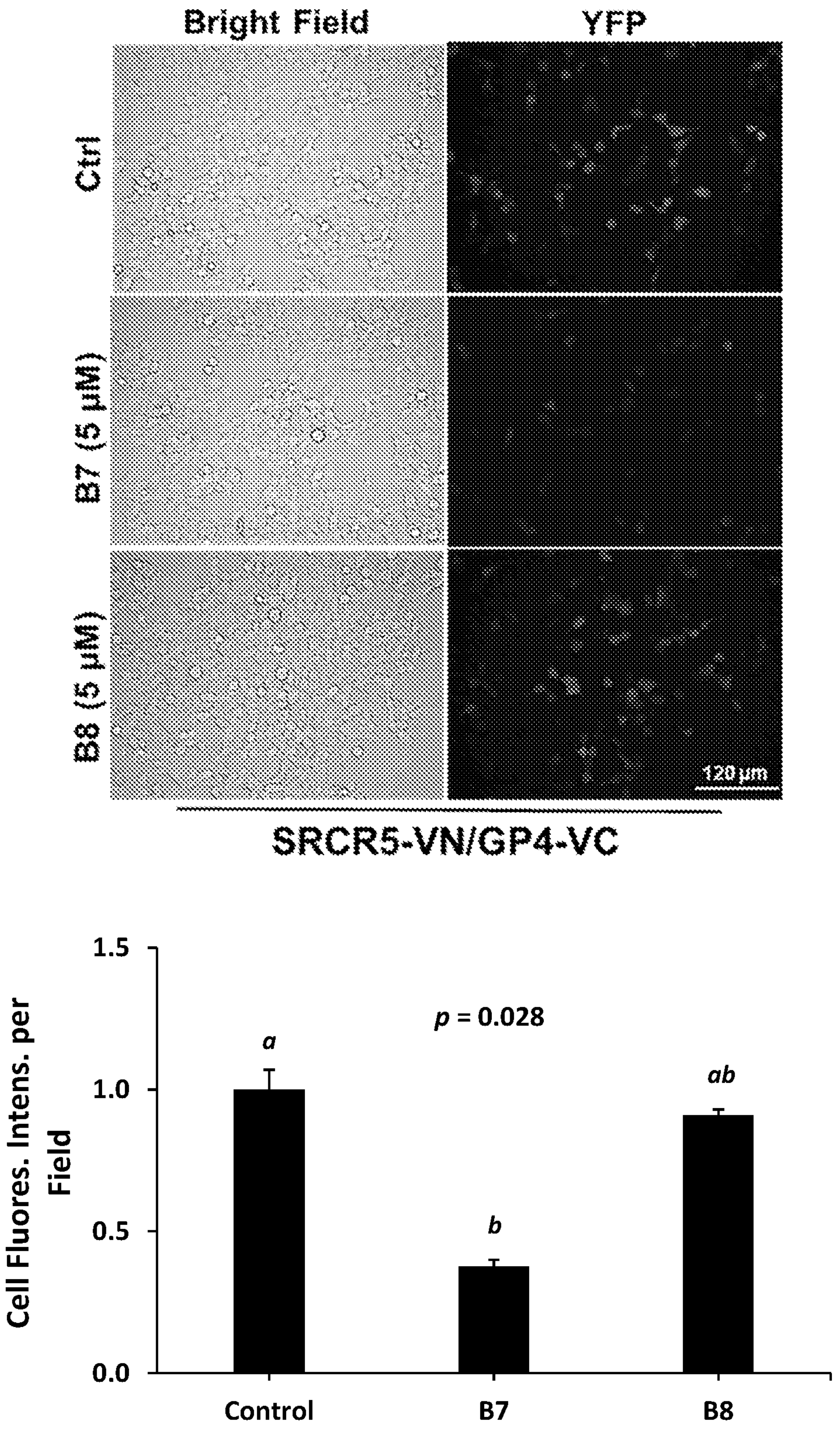
Figure 3:
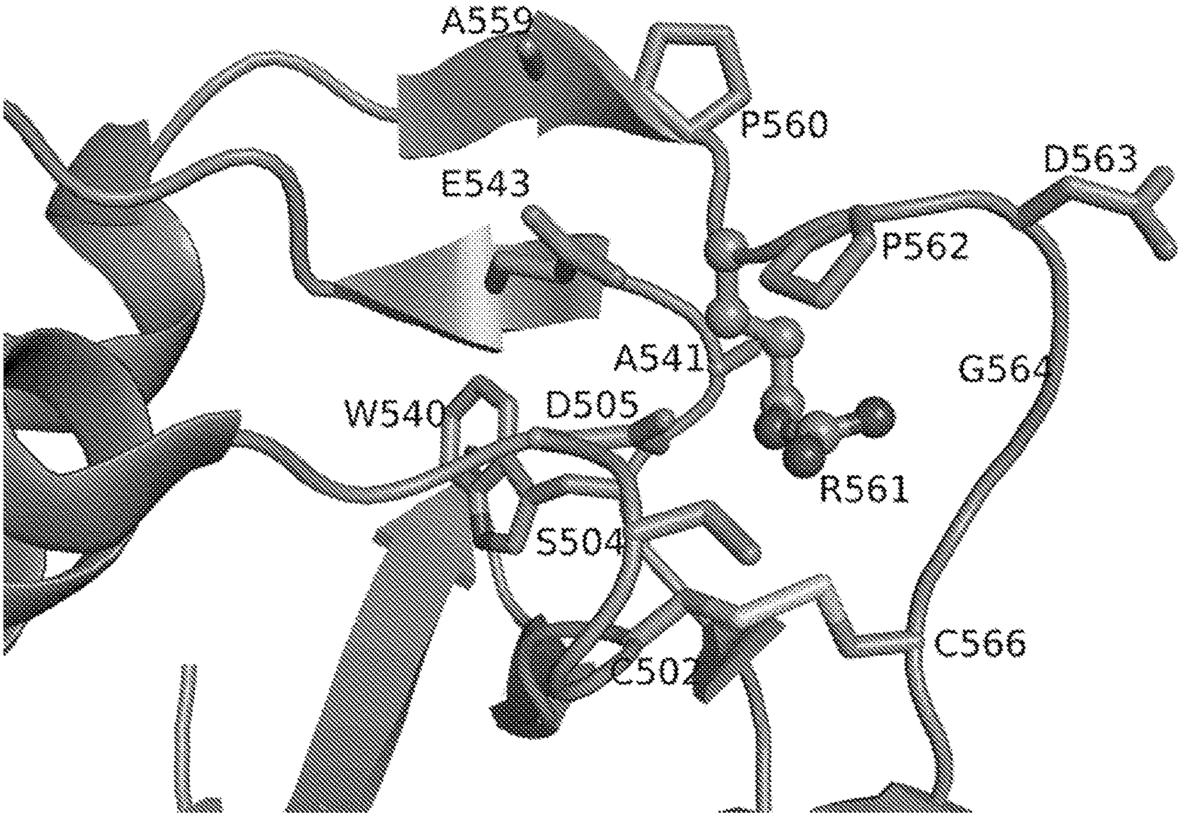
FIG. 3 shows the CD163 target site (with residues shown) for virtual screening.

The BiFC assays was tested to determine whether it could identify small molecules with potential to block the protein-protein interactions between CD163 and PRRSV. A customized virtual screen of a library of commercially available small molecules was performed with the AtomNet® model at a region centered around R561 (FIG. 3) based on the available 3-D protein structure of porcine CD163-SRCR5 domain, and 74 compounds predicted to target this potential binding site were procured. Ma et al., *J. Virol.* 91(3): e01897-16 (2017). These compounds were tested using the BiFC assay, to evaluate their ability to inhibit the PPI between GP2a and SRCR5. Plasmids were co-transfected in HEK293T cells, 4 h later, compounds were individually administered to cells at 5 μM. Twenty-four hours later, images were taken under a fluorescence microscope and the fluorescence quantified. Of all 74 compounds, 1 positive hit was identified, named herein as B7 (4-fluoro-2-methyl-N-[3-(3-morpholin-4-ylsulfonylanilino)quinoxalin-2-yl]benzenesulfonamide, FIG. 1D, Table 2) that significantly inhibited the reconstitution of venus fluorescence in the BiFC assay (FIG. 1E). Using the other BiFC assay, it was further verified that B7 also inhibited the PPI between PRRSV GP4 glycoprotein and CD163-SRCR5 domain (FIG. 1F). Until these studies, there has been no known biological activity reported for compound B7.

TABLE 2

| B7 and Analogus Compounds | | |
|---|---|---|
| ID | Name | Structure |
| B7 | 4-fluoro-2-methyl-N-[3-(3-morpholin-4-ylsulfonylanilino) quinoxalin-2-yl] benzenesulfonamide | 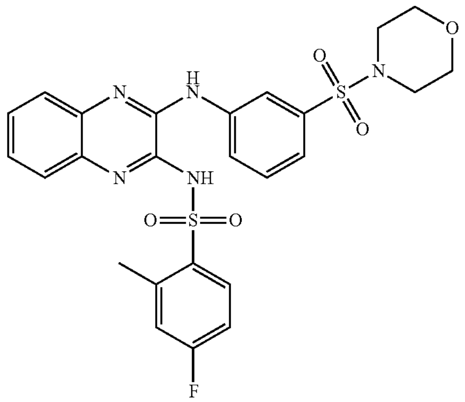 [SMILES: Cc1cc(F)ccc1S(=O)(=O)Nc1nc2ccccc2nc1Nc1cccc(S(=O)(=O)N2CCOCC2)c1] |
| B7-A1 | N-[3-(4-chloro-3-morpholin-4-ylsulfonylanilino)quinoxalin-2-yl] benzenesulfonamide | 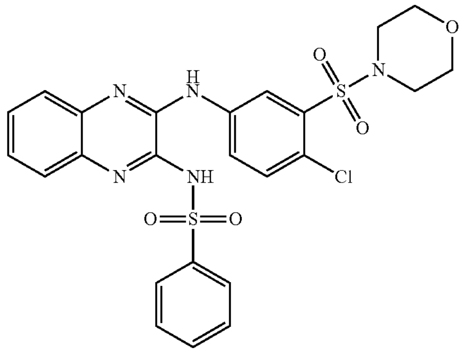 [SMILES: O=S(=O)(Nc1nc2ccccc2nc1Nc1ccc(Cl)c(S(=O)(=O)N2CCOCC2)c1)c1ccccc1] |
| B7-A2 | 2-methyl-N-[3-(4-morpholin-4-ylsulfonylanilino)quinoxalin-2-yl] benzenesulfonamide | 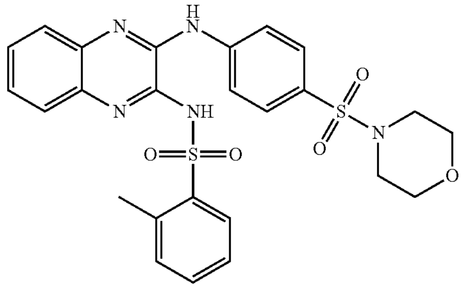 [SMILES: Cc1ccccc1S(=O)(=O)Nc1nc2ccccc2nc1Nc1ccc(S(=O)(=O)N2CCOCC2)cc1] |

TABLE 2-continued
| ID | Name | Structure |
|---|---|---|
| | B7 and Analogus Compounds | |
| B7-A3 | N-[3-(3-morpholin-4-ylsulfonylanilino)quinoxalin-2-yl] benzenesulfonamide | 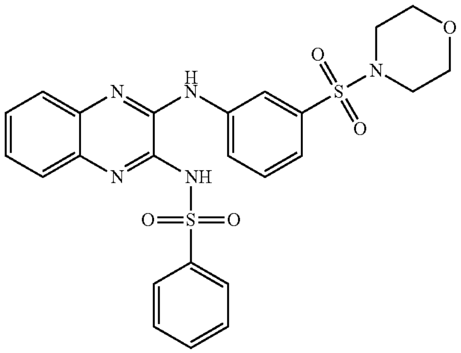 [SMILES: O=S(=O)(Nc1nc2ccccc2nc1Nc1cccc(S(=O)(=O)N2CCOCC2)c1)c1ccccc1] |
| B7-A4 | 4-methyl-N-[3-(3-piperidin-1-ylsulfonylanilino)quinoxalin-2-yl] benzenesulfonamide | 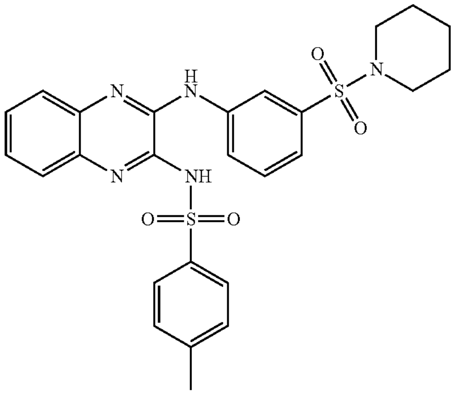 [SMILES: Cc1ccc(S(=O)(=O)Nc2nc3ccccc3nc2Nc2cccc(S(=O)(=O)N3CCCCC3)c2)cc1] |
| B7-A5 | 4-methyl-N-(3-morpholinoquinoxalin-2-yl)benzenesulfonamide | 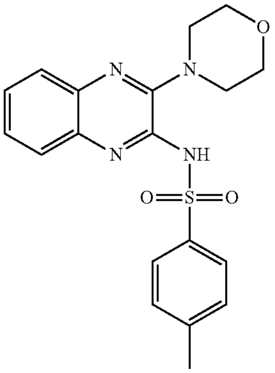 [SMILES: Cc1ccc(S(=O)(=O)Nc2nc3ccccc3nc2N2CCOCC2)cc1] |
| B7-A6 | 2-methyl-N-(3-morpholin-4-ylquinoxalin-2-yl) benzenesulfonamide | 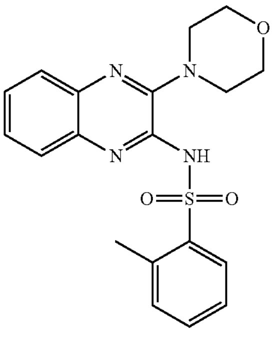 [SMILES: Cc1ccccc1S(=O)(=O)Nc1nc2ccccc2nc1N1CCOCC1] |

TABLE 2-continued

B7 and Analogus Compounds

| ID | Name | Structure |
|---|---|---|
| B7-A7 | 3-(morpholinosulfonyl)aniline | 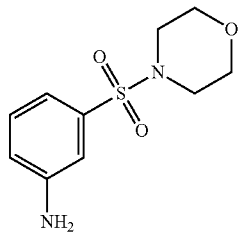 [SMILES: Nc1cccc(S(=O)(=O)N2CCOCC2)c1] |
| B7-A8 | 1-tosylpiperidine | 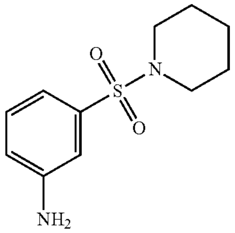 [SMILES: Nc1cccc(S(=O)(=O)N2CCCCC2)c1] |

Inhibition of the PRRSV Infection of PAMs by Compound 87

Figure 4:
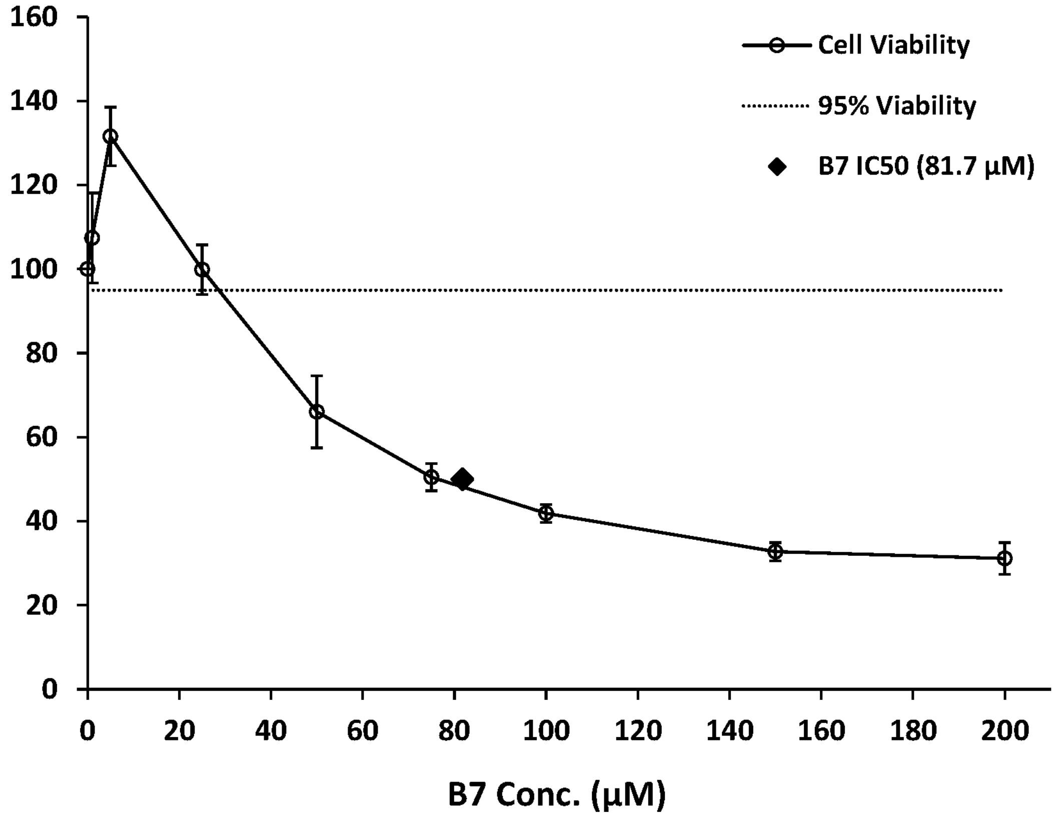
FIG. 4 shows a plot of the cell viability versus the B7 concentration in the MTT assay of the B7 incubated with porcine alveolar macrophages (PAMs) for 24 h. The B7 $IC_{50}$ of 81.7 μM is indicated. Mean±SD, n=3.
Figure 5A:
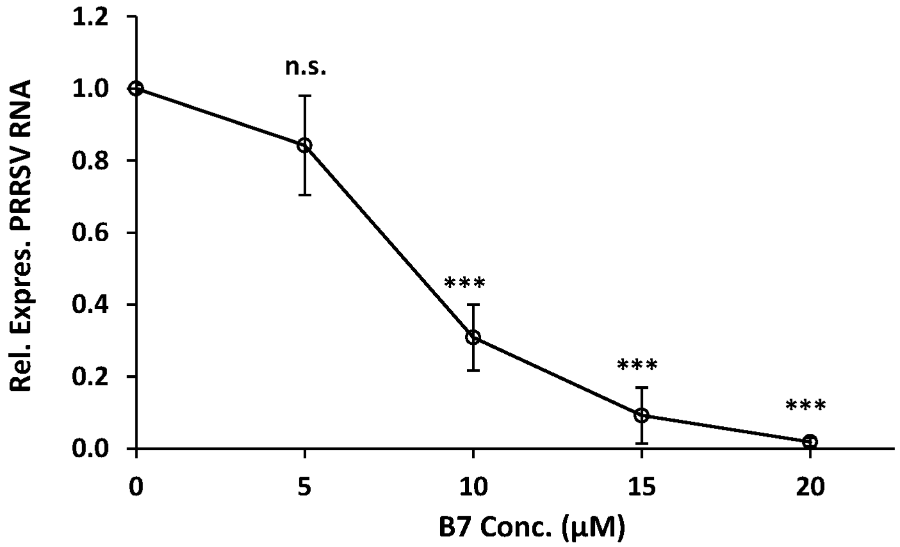
FIGS. 5A-D show inhibition of the PRRSV infection of PAMs by compound B7.
Figure 5B:
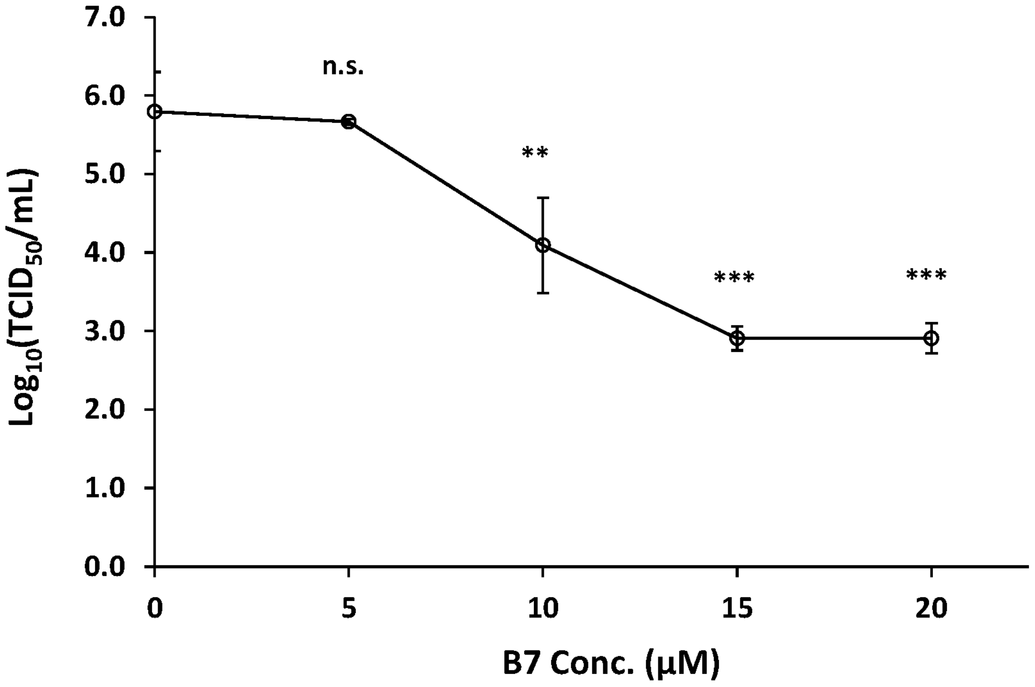

Based on the demonstrated inhibitory effect of B7 on the interaction between CD163-SRCR5 domain and PRRSV glycoproteins, this compound was tested to determine whether it would inhibit the PRRSV infection of PAMs. MTT assay revealed that the B7 compound is well-tolerated by PAMs at concentrations below 25 μM, with the $LC_{50}$ calculated to be 81.7 μM (FIG. 4). Finney, *Probit Analysis* ($2^{nd}$ ed.) 78(3): 388-390 (1952). Primary PAMs were then pre-treated with B7 ranging from 0, 5, 10, 15, to 20 μM for 4 h, followed by 1 h inoculation with PRRSV strain VR-2332 (MOI=0.1). The infected PAMs were then continuously incubated with different concentrations of B7. At 24 h after inoculation, total RNAs were extracted from PAMs. Quantitative reverse transcription PCR (qRT-PCR) revealed a dose-dependent inhibition of PRRSV infection of PAMs by the B7 treatment (FIG. 5A). Titration of PRRSV from the culture media of the infected PAMs further confirmed that 10-20 μM B7 inhibited PRRSV infection of PAMs effectively, with 1.7 and 2.9 log reduction of viral titer by 10 and 15 μM B7 treatment, respectively (FIG. 5B).

Figure 5C:
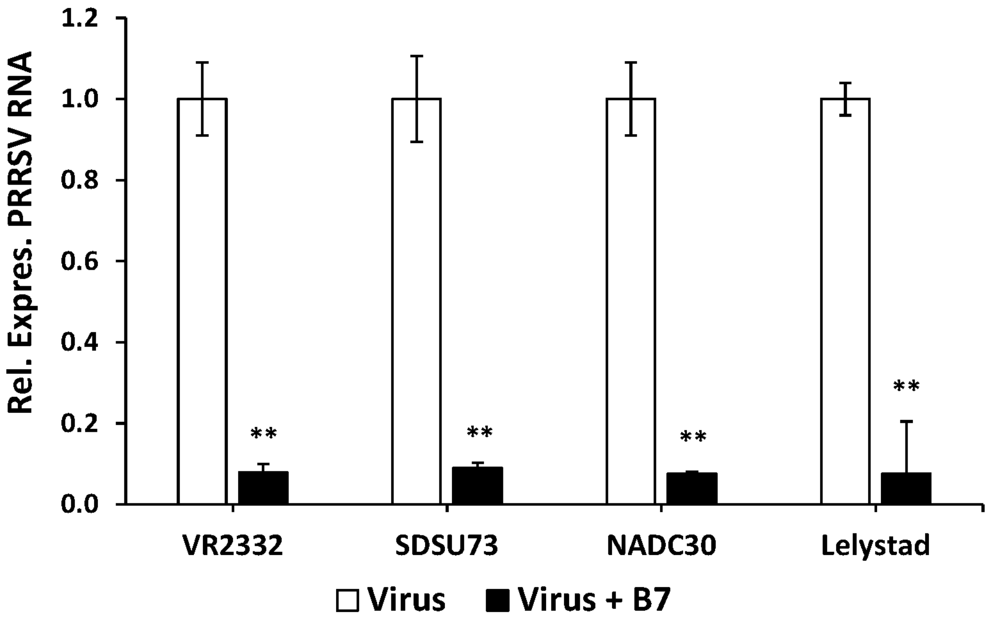
Figure 5D:
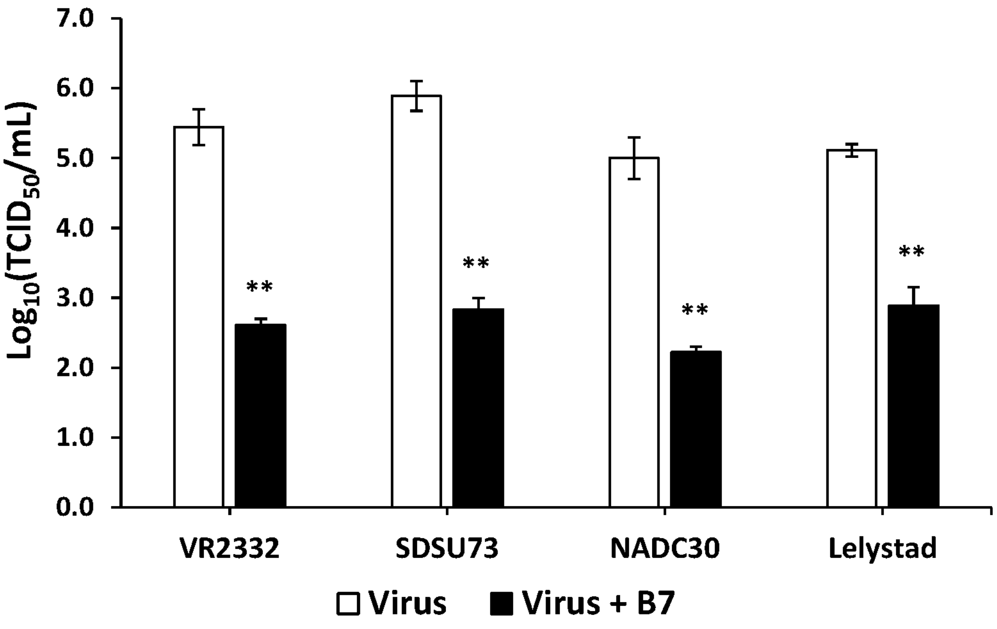

The inhibitory effect of B7 was further tested on multiple strains of PRRSV. PAMs were pre-treated with 15 μM B7 for 4 h, and inoculated with PRRSV strains VR-2332, SDSU73, NADC30 (Type II), or Lelystad (Type I) for 1 h, and continuously incubated with 15 μM B7 for 24 h. qRT-PCR revealed that B7 treatment significantly decreased the viral RNA detected in infected PAMs by all PRRSV strains (FIG. 5C). This inhibitory effect is further confirmed by viral titration results for the culture media of infected PAMs, with 2.8-3.1 log reduction of viral titers across the 3 Type II PRRSV strains and 2.2 log reduction of viral titer for the type I strain (Lelystad) by 15 μM B7 treatment (FIG. 5D). Thus, compound B7 indeed inhibits the PRRSV infection of PAMs. The significant dosage-dependent inhibition by B7 to PRRSV infection of PAMs makes this compound and its derivatives clear candidates for evaluating further their in vivo efficacy in inhibiting PRRSV infection.

Evaluating the PRRSV Infection Inhibitory Effect for Compounds with Similar Chemical Structure as B7

Figure 6A:
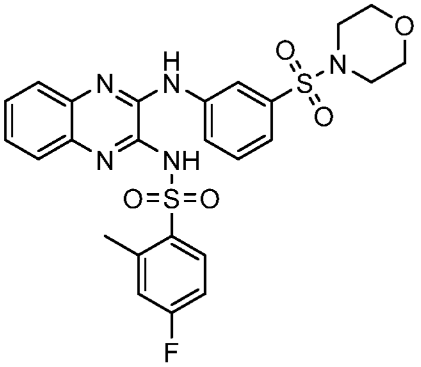
FIGS. 6A-B show the evaluation of the PRRSV inhibitory effect for compounds structurally similar to B7.
Figure 6A:
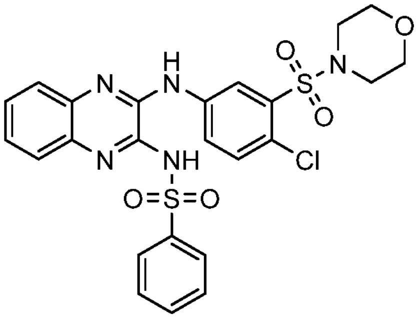
Figure 6A:
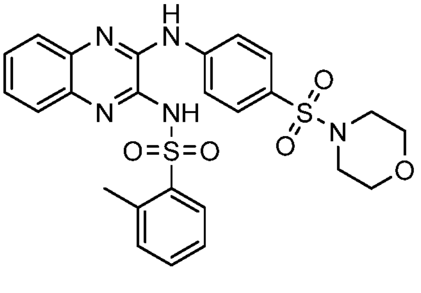
Figure 6A:
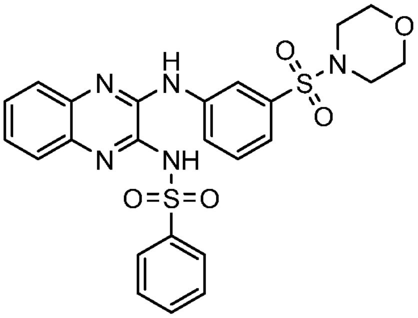
Figure 6A:
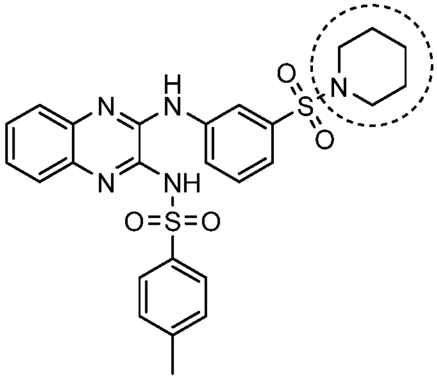
Figure 6A:
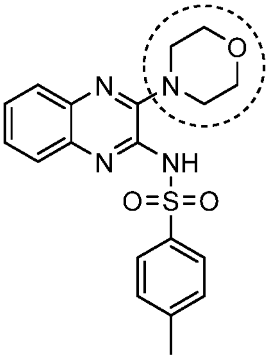
Figure 6A:
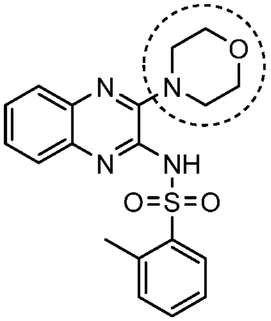
Figure 6B:
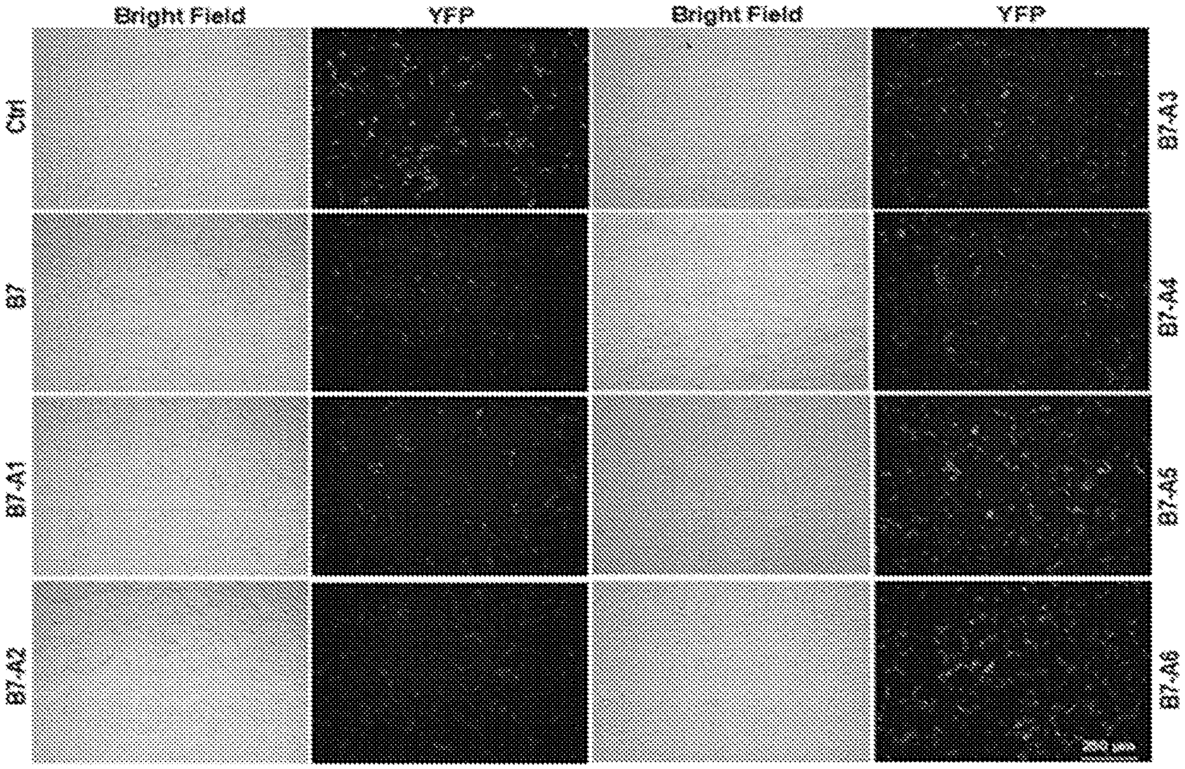
Figure 7A:
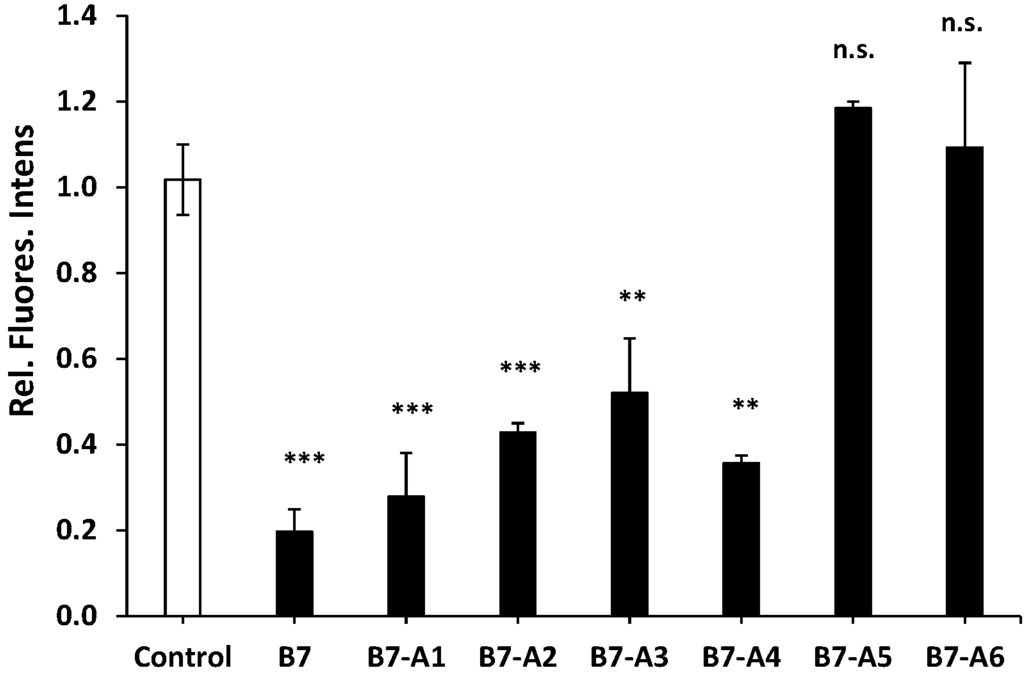
FIGS. 7A-C show the PRRSV inhibitory effect for compounds structurally similar to B7.

B7 is a synthetic compound with a previously unverified function. In order to examine the structural relevance of the B7 scaffold for PRRSV infection inhibition, a PubChem search was performed, and 6 compounds structurally related to B7 were identified (named herein as B7-A1 to B7-A6, FIG. 6A, Table 2). The BiFC assay was used to check if any of these B7 analogues can inhibit the protein-protein interactions (PPI) between CD163-SRCR5 domain and PRRSV GP2a protein. Similar to B7, compounds B7-A1 to B7-A4 all significantly inhibited the CD163-SRCR5/GP2a PPI in the BiFC assay (FIG. 6B, FIG. 7A). Interestingly, shifting the 3-(morpholinosulfonyl)anilino moiety of B7 to 4-(morpholinosulfonyl) anilino position (B7-A2), or changing this moiety to 3-(piperidinylsulfonyl)anilino group (B7-A4; FIG. 6A, hashed circle) does not eliminate these compounds' ability to inhibit the CD163-SRCR5/GP2a PPI (FIG. 6B, FIG. 7A). However, replacing the 3-(piperidinylsulfonyl)anilino or 3-(morpholinosulfonyl)anilino moiety by morpholine in compounds B7-A5 and B7-A6 (FIG. 6A, hashed circles) completely blocked their ability to inhibit the CD163-SRCR2/GP2a interaction (FIG. 6B, FIG. 7A). The BiFC assays reported here would be of great value for further screening of small molecules that could block the PPIs between PRRSV and CD163.

Figure 7B:
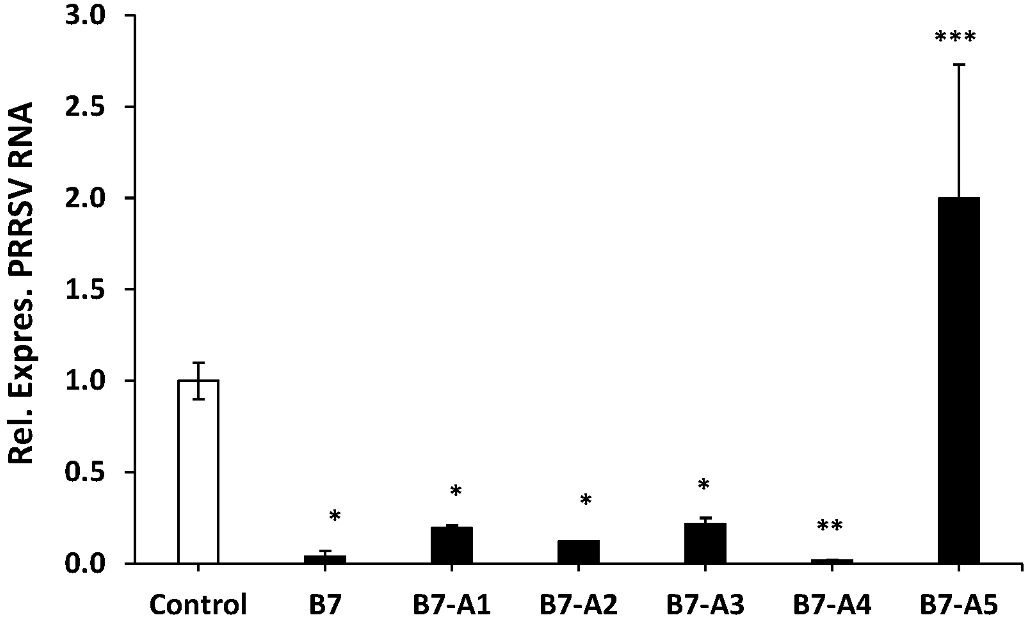
Figure 7C:
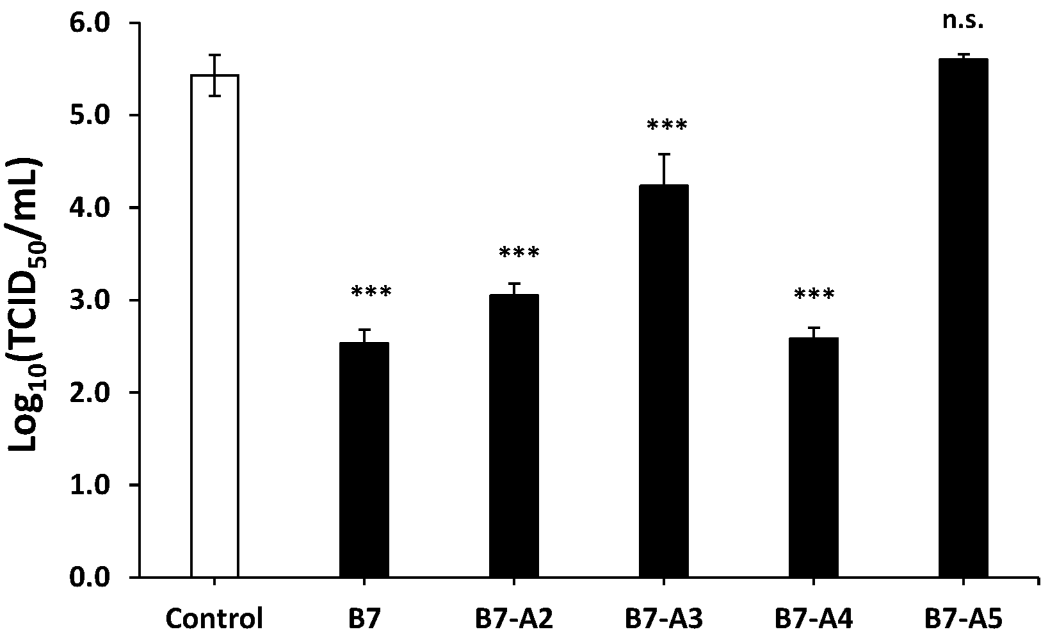
Figure 8:
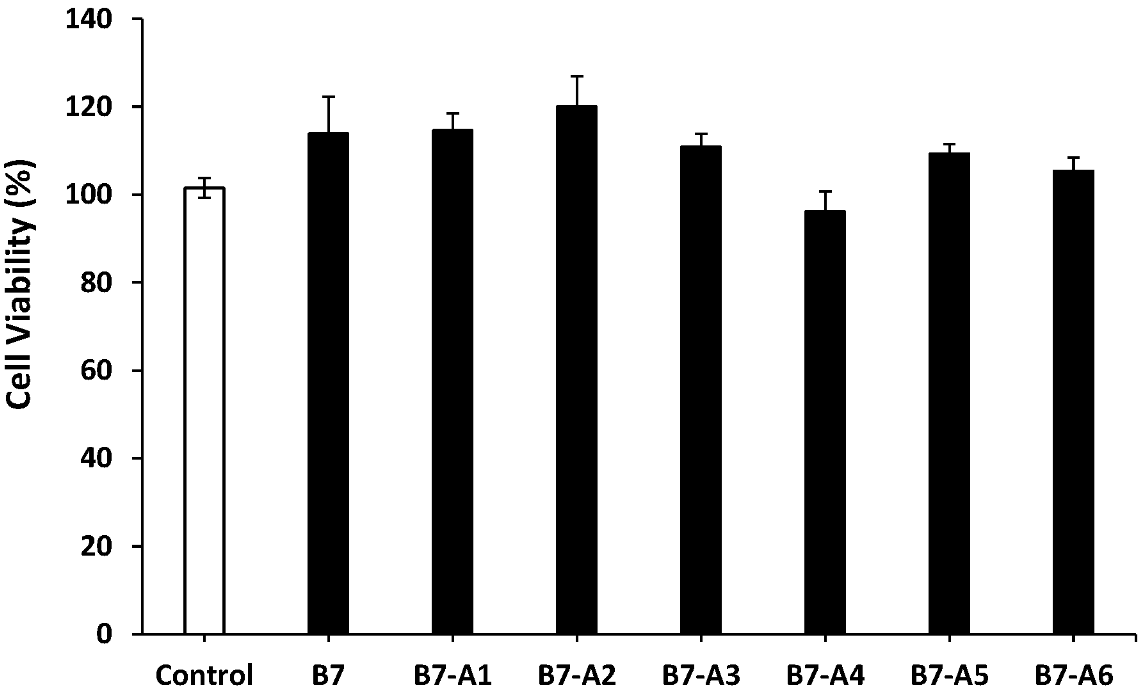
FIG. 8 shows results from an MTT assay of the B7 and its analogue compounds incubated with PAMs for 24 h. Bar=mean±SD, n=3.

In order to confirm the function of these compounds, compounds B7-A1 through B7-A5 were further evaluated on PRRSV infection of PAMs. MTT assay revealed that these compounds have no obvious cytotoxic effect on PAMs at 15 μM level (FIG. 8). PAMs were then pre-treated with 15 μM of each compound for 4 h and inoculated with PRRSV strain VR-2332 for 1 h. The cells were then continuously incubated with 15 μM of the same compound. At 24 h, total RNAs were extracted from infected PAMs and qRT-PCR demonstrated that similar to B7, compounds B7-A1 to B7-A4 all significantly inhibited the PRRSV RNA level in treated PAMs compared with the control (FIG. 7B). Also, consistent with the BiFC results, treatment with B7-A5 failed to inhibit PRRSV RNA level in infected PAMs (FIG. 7B). Titration of the 24 h culture media of infected cells further confirmed the finding by demonstrating that compounds B7-A1 through B7-A4 but not B7-A5 all inhibited PRRSV infection of PAMs, with 2.2, 2.4, 1.2, and 2.8 log reduction of viral titer by compounds B7-A1 through A4 treatment, respectively (FIG. 7C). Taken together, the results indicate that the 3-(morpholinosulfonyl)anilino moiety (in B7 and B7-A1 through B7-A3) and the 3-(piperidinylsulfonyl)anilino moiety (in B7-A4) are important for the inhibitory effect of these compounds on PRRSV infection.

Figure 9A:
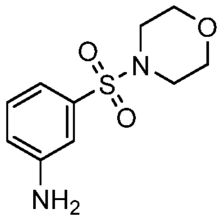
FIGS. 9A-D shows that 3-(morpholinosulfonyl)anilino or 3-(piperidinylsulfonyl)anilino alone does not inhibit PRRSV infection and B7 post-treatment significantly inhibits PRRSV infection.
Figure 9A:
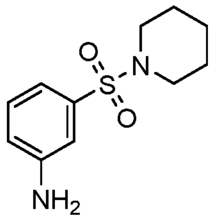
Figure 9B:
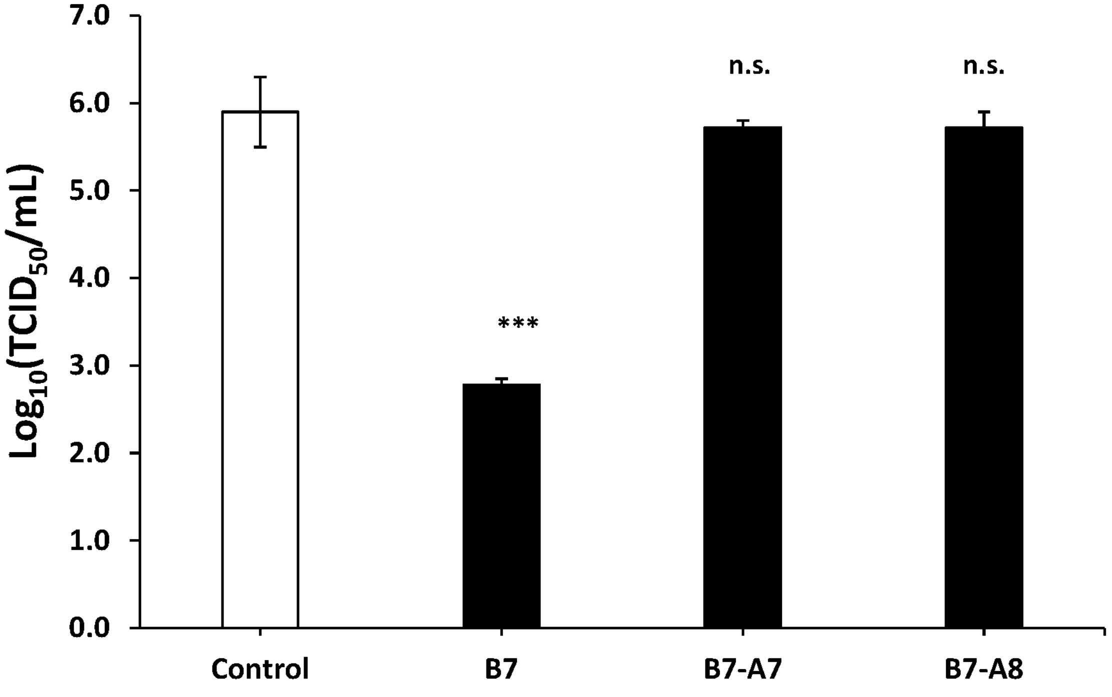

The 3-(Morpholinosulfonyl)Anilino or 3-(Piperidinylsulfonyl)Anilino Alone does not Inhibit PRRSV Infection and Post-Treatment with 87 Significantly Inhibits PRRSV Infection It was also noticed that removing the methyl and/or fluoro groups from the benzenesulfonamide moiety of B7 (compound B7-A1, A2, and A3, FIG. 6A) weakened the compound's inhibitory function in BiFC assay (FIG. 6B, 7A) and PRRSV infection assay (FIG. 7B, 7C), although the effect is not as dramatic as modifying the 3-(morpholinosulfonyl) anilino moiety. In order to determine if the 3-(morpholinosulfonyl)anilino or 3-(piperidinylsulfonyl)anilino chemical group alone would be sufficient to suppress PRRSV infection, these 2 compounds were purchased and were named B7-A7 and B7-A8, respectively (FIG. 9A). PAMs were treated with 15 μM of each molecule for 4 h then followed by 1 h PRRSV VR-2332 inoculation. The cells were then incubated with the same compound for 24 h. Titration of PRRSV from the culture media of treated cells revealed that none of these 2 compounds inhibited PRRSV infection of PAMs (FIG. 9B). Therefore, while these 2 moieties are functionally critical, the presence of other moieties (e.g., benzenesulfonamide) are also essential for the inhibition of PRRSV infection.

Figure 9C:
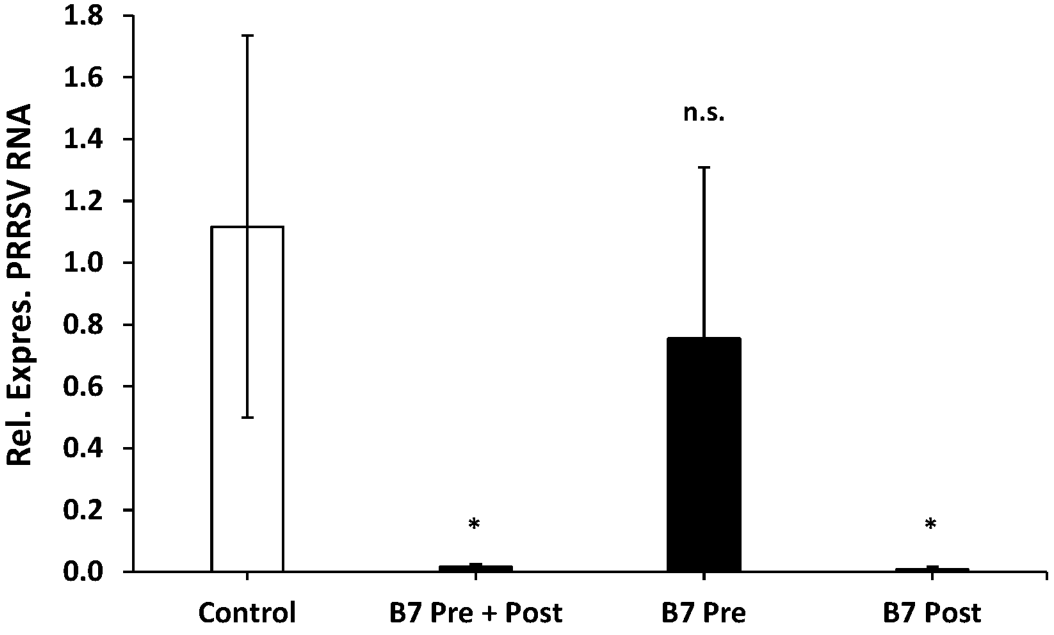
Figure 9D:
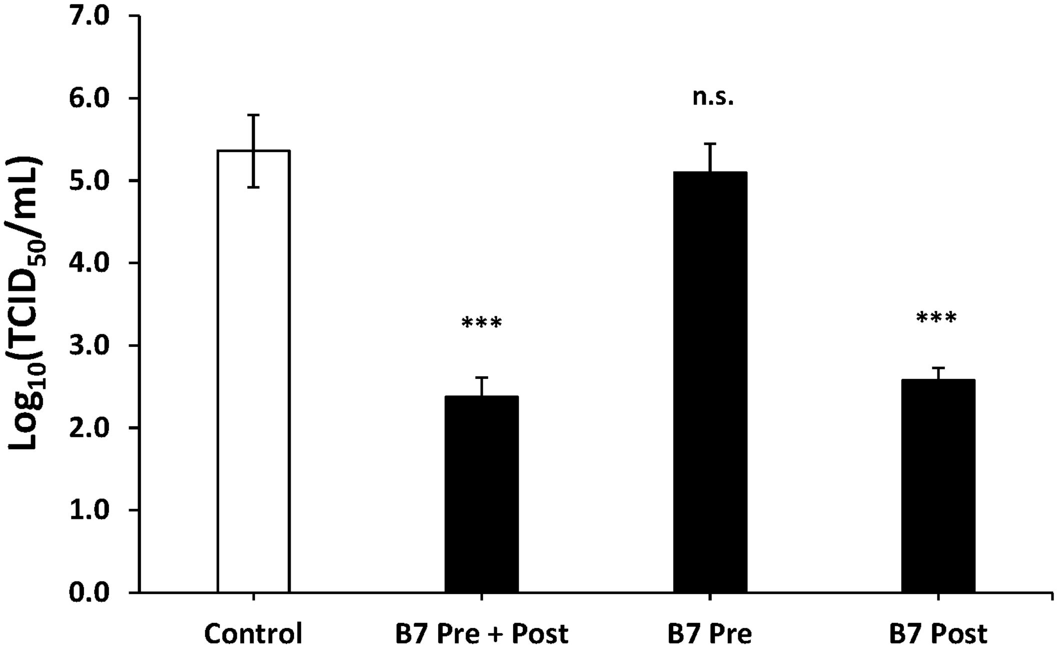
Figure 10A:
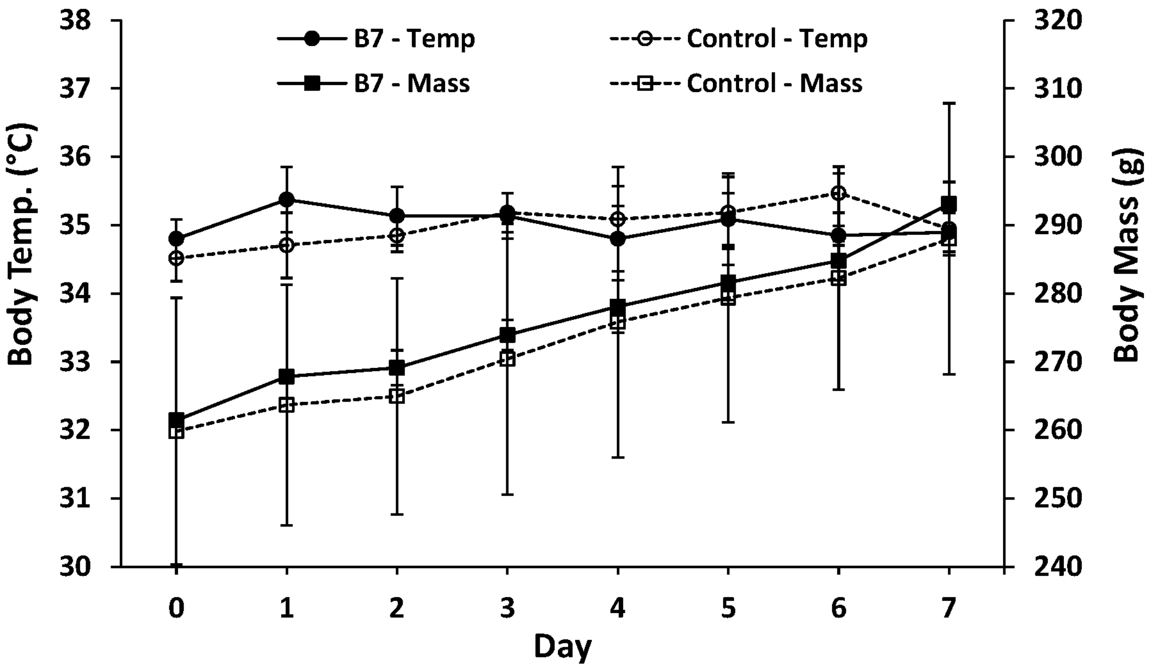
FIGS. 10A-B show results from a rat acute toxicity study with B7 IM injection (4 mg/kg).
Figure 10B:
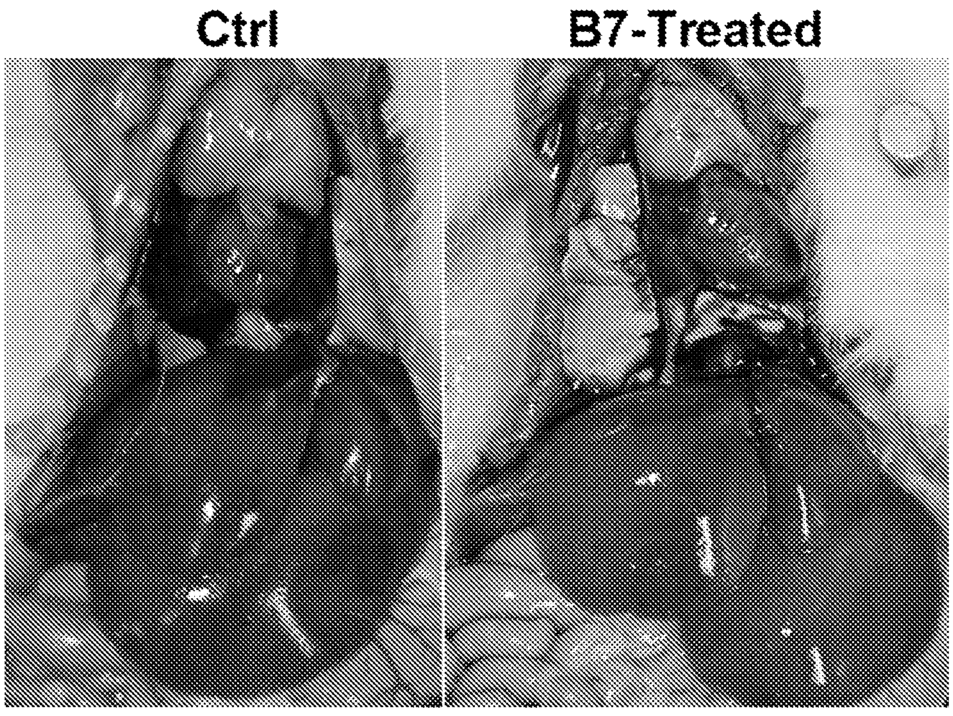
Figure 11A:
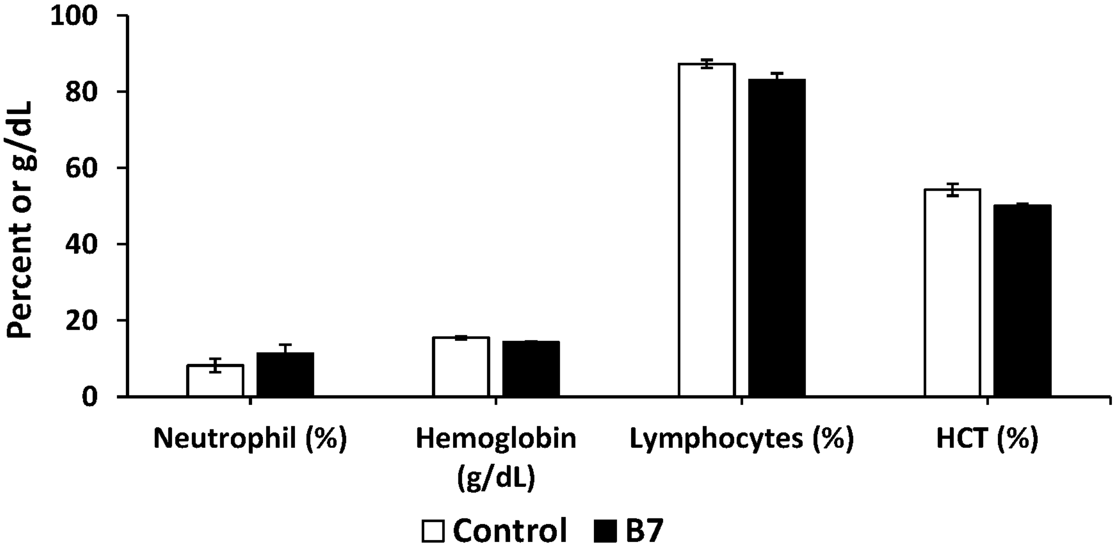
FIGS. 11A-B show complete blood count parameters with statistical significance from rats injected with control or B7.
Figure 11B:
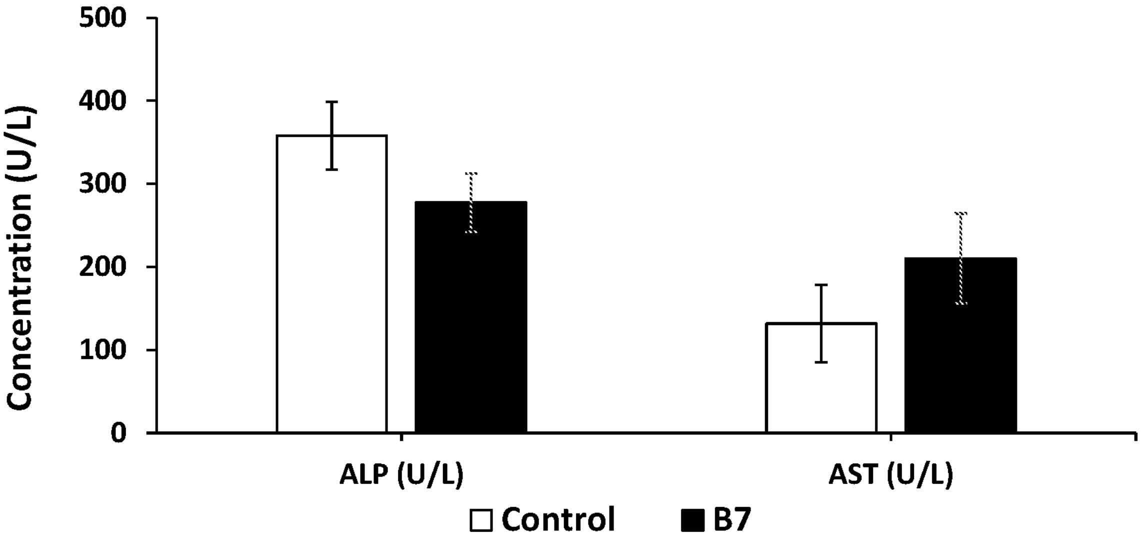

Having verified the inhibitory effect of B7 on PRRSV infection upon pre- and post-inoculation treatment, experiments were performed to determine whether treatment with B7 either pre- or post-inoculation alone would have a significant effect. PAMs were treated either with B7 for 4 h only and followed by 1 h PRRSV strain VR-2332 inoculation with no post-treatment, or with only 24 h post-PRRSV inoculation treatment without pre-treatment. At 24 h post infection, the viral RNA in PAMs and the PRRSV titer in culture media were evaluated. qRT-PCR revealed that while post-treatment alone by B7 exhibited a similar inhibitory effect as the pre-plus post-treatment on PRRSV infection, while pre-treatment had a minimal impact (FIG. 9C). This is further confirmed by the viral titration for the culture media of infected PAMs, with compound B7 post-inoculation treatment alone resulted in 2.8 log reduction of PRRSV titer (FIG. 9D). This indicates that there is a reversible association between B7 compound and the CD163-SRCR5 protein domain, which could no longer block the interaction between PRRSV glycoproteins and CD163-SRCR5 upon the removal of B7 compound by washing. Further refined structure activity relationship analysis may be useful to unveil the nature of B7 and SRCR5 molecular-molecular association. These findings, along with a full understanding of the key residues in CD163-SRCR5 domain involved in PRRSV recognition, may provide pertinent information for the targeted screen of effective compounds against PRRS.

Example 3

Rat Acute Toxicity Study

A single dose pilot toxicity study of the compound B7 was performed using laboratory rats. The study was conducted as:

1. Eight 10-week Sprague Dawley laboratory male rats (~260 g each) were randomly selected into two groups (n=4), with group 1 for control and group 2 for B7-treatment.
2. Day 0, injection of B7 drug. The intramuscular (IM) injection was vehicle for group 1, and 4 mg/kg B7 per rat for group 2, with 0.15 mL of volume per rat, to the left thigh region. The B7 was dissolved in vehicle containing 30% DMSO and 50% propylene glycol (PG), and 20% 20 mM Tris·HCl, pH 8.0.
3. Days 1-7 observation of rats with daily body weight and temperature measurement and making records of any abnormal behavior.
4. Day 7 necropsy: Euthanize the rats with $CO_2$, immediately followed by blood sample collection from heart. Conduct postmortem rat gross-anatomic pathology analysis (brain, heart, lung, liver, kidney, spleen).
5. Conduct clinical pathology analysis (CBC/Chemistry by IDDEX Bioanalytics) for the collected blood samples.

Results

No signs of abnormality were observed for the control group (C1-C4) and B7 treatment group (T1-T4) during the 7-day study, with normal daily weigh gain and body temperature found in these rats. Gross pathology analysis on these rats found that there were multifocal to coalescing mild pale tan discoloration on the surface of liver of C2, T3 and T4; these pale areas of discolorations did not extend into the parenchyma. There was also an enhanced reticular pattern in all 3 rats. Additionally, in T4 the cortical surface of kidney had multiple, mild tan discolorations. These could be euthanasia artifacts, incidental lesions, or could represent real pathological changes. The whole blood analysis (Table 3) revealed no obvious change for blood cell counts between control and B7-treatment groups, with all values fall within or close to the normal ranges as described elsewhere. He et al., *PLoS One* 12: e0189837 (2017); Delwatta et al., *Anim. Mod. Exp. Med.* 1: 250-254 (2018).

TABLE 3

Blood Parameters for Sprague Dawley Male Rats Administered Control or B7 (4 mg/kg) (n = 4 each)

| Blood Serum Parameter | Control | Std Dev | B7 | Std Dev |
|---|---|---|---|---|
| Neutrophil (%) | 8.2 | 1.8 | 11.4 | 2.3 |
| Neutrophil (/μL) | 561.5 | 191.8 | 425.0 | 71.0 |
| WBC (K/μL) | 7.5 | 3.9 | 3.8 | 0.7 |
| RBC (M/μL L) | 8.3 | 0.5 | 7.6 | 0.1 |
| HGB (g/dL) | 15.5 | 0.5 | 14.4 | 0.2 |
| Lymphocyte (/μL) | 6553.0 | 3474.5 | 3188.0 | 667.0 |
| Lymphocytes (%) | 87.3 | 1.0 | 83.1 | 1.7 |
| HCT (%) | 54.3 | 1.6 | 50.1 | 0.6 |
| Monocyte (/μL) | 307.3 | 199.9 | 179.5 | 32.7 |
| Monocytes (%) | 3.9 | 0.8 | 4.8 | 0.7 |
| Eosinophil (/μL) | 29.5 | 23.8 | 19.0 | 15.9 |
| Eosinophils (%) | 0.4 | 0.2 | 0.5 | 0.4 |
| MCV (fL) | 66.0 | 2.9 | 65.8 | 1.3 |
| Basophil (/μL) | 23.5 | 24.2 | 13.5 | 16.1 |
| Basophils (%) | 0.3 | 0.2 | 0.3 | 0.4 |
| MCH (pg) | 18.8 | 0.7 | 18.9 | 0.3 |
| MCHC (g/dL) | 28.5 | 0.1 | 28.7 | 0.1 |
| ALP (U/L) | 358.0 | 40.9 | 277.5 | 35.0 |
| AST (U/L) | 131.8 | 46.8 | 210.3 | 54.2 |
| ALT (U/L) | 73.0 | 13.9 | 95.5 | 22.4 |
| Creatine kinase (U/L) | 318.0 | 167.7 | 585.5 | 352.4 |
| Albumin (g/dL) | 3.6 | 0.1 | 3.5 | 0.1 |
| Total Bilirubin (mg/dL) | 0.1 | 0.1 | 0.1 | 0.0 |
| Total Protein (g/dL) | 6.5 | 0.1 | 6.4 | 0.1 |

TABLE 3-continued

Blood Parameters for Sprague Dawley Male Rats Administered Control or B7 (4 mg/kg) (n = 4 each)

| Blood Serum Parameter | Control | Std Dev | B7 | Std Dev |
|---|---|---|---|---|
| Globulin (g/dL) | 2.9 | 0.0 | 2.9 | 0.1 |
| Bilirubin - Conjugated (mg/dL) | 0.0 | 0.0 | 0.0 | 0.0 |
| BUN (mg/dL) | 17.5 | 1.3 | 16.8 | 1.0 |
| Creatinine (mg/dL) | 0.3 | 0.0 | 0.2 | 0.1 |
| Cholesterol (mg/dL) | 73.0 | 8.3 | 76.0 | 12.7 |
| Glucose (mg/dL) | 260.3 | 96.3 | 175.5 | 80.8 |
| Calcium (mg/dL) | 12.3 | 0.5 | 11.8 | 0.8 |
| Phosphorus (mg/dL) | 12.9 | 0.9 | 13.0 | 1.1 |
| Bicarbonate $TCO_2$ (mmol/L) | 30.3 | 1.5 | 32.8 | 2.2 |
| Chloride (mmol/L) | 96.8 | 0.5 | 97.0 | 0.8 |
| Potassium (mmol/L) | 7.1 | 0.7 | 6.7 | 1.4 |
| ALB/GLOB ratio | 1.3 | 0.1 | 1.2 | 0.1 |
| Sodium (mmol/L) | 145.0 | 1.4 | 145.8 | 1.0 |
| BUN/Creatinine Ratio | 58.3 | 4.3 | 76.7 | 14.1 |
| Bilirubin - Unconjugated (mg/dL) | 0.1 | 0.1 | 0.1 | 0.0 |
| NA/K Ratio | 20.8 | 2.2 | 22.3 | 4.3 |
| Hemolysis Index | Normal | – | + | – |
| Lipemia Index | Normal | – | Normal | – |

TABLE 4

Statistically Significant CBC Parameters

| | Neutrophils (%) | HGB (g/dL) | Lymphocytes (%) | HCT (%) |
|---|---|---|---|---|
| Control Mean | 8.2 | 15.475 | 87.325 | 54.325 |
| Control Std. Dev. | 1.79 | 0.45 | 1.03 | 1.56 |
| B7 Mean | 11.35 | 14.35 | 83.125 | 50.075 |
| B7 Std. Dev. | 2.31 | 0.17 | 1.74 | 0.61 |
| p-value | 0.036 | 0.026 | 0.006 | 0.023 |
| Range | 6.14-22.95 | 13.5-15.9 | 69.68-86.89 | 42-49 |

| | ALP (U/L) | AST (U/L) |
|---|---|---|
| Control Mean | 358 | 131.75 |
| Control Std. Dev. | 40.88 | 46.75 |
| B7 Mean | 277.5 | 210.25 |
| B7 Std. Dev. | 34.97 | 54.17 |
| p-value | 0.023 | 0.036 |

For the blood chemistry analysis, only ALP and AST were changed slightly with statistical significances. Table 3. However, the normal ranges described in the literature for male Sprague Dawley rats varies considerably. Two experienced laboratory animal veterinarians were consulted. Based on their assessment of the data, there are no signs of acute toxicity in these rats. A clinical pathologist reached the same conclusion and pointed out that the increase in AST in treatment group most likely resulted from hemolysis of the blood samples, which is also seen in one control sample with high AST. The hemolysis of the blood samples did not happen in vivo based on the normal Bilirubin level for all samples. This could be result of in vitro sample handing, such as the sheering force for blood-withdrawal or contamination of blood cells in serum samples.

Example 4

Pig Acute Toxicity Study

A single-dose pilot study in pigs is being conducted to determine the acute toxicity at two dosage levels: a low dose of 10 mg/10 kg and a high dose of 40 mg/10 kg B7. This counts for an estimated 27.6 μM or 110.4 μM maximum plasma concentration of B7 in pigs, respectively, assuming 100% bioavailability. The n=3 will be used for this pilot pig toxicity study based on previous description on exploratory drug safety study in large animals. See Bass et al., *J. Pharmacol. Toxicol. Met.* 60: 69-78 (2009).

The study will be conducted as:

1. Nine 4-week old male piglets are randomly separated into 3 groups (n=3), with group 1 for control, group 2 and 3 for two different doses of B7-treatment.
2. Day 0, injection of B7 drug. The IM injection will be in a vehicle containing 30% DMSO and 50% propylene glycol (PG), and 20% 20 mM Tris·HCl, pH 8.0 for group 1, and 10 or 40 mg B7 for groups 2 and 3, respectively, with 2.5 mL of injection volume. The injection site is the rump and ham region of the piglets.
3. Days 1-7 observation of pigs, blood sample collection on days 0, 1, 2, 3, 5, and 7. The B7 blood plasma levels will be measured using LC-MS for pharmacokinetics analysis.
4. Day 7 necropsy: Pigs will be anesthetized with Telazol 4.4 mg/Kg, Ketamine 2.2 mg/kg and Xylazine 4.4 mg/kg and euthanized with a Pentobarbital overdose (100 mg/Kg). Blood samples will be collected for clinical pathology analysis by IDDEX Bioanalytics. Postmortem gross-anatomic pathology analyses of the brain, heart, lung, liver, kidney, and spleen will be conducted.
5. Microscopic pathological analyses will be conducted on collected organs/tissues to survey for any indication of acute toxicity based on gross-pathology and blood chemistry data.

Pig PRRSV Challenge Study with B7

For the efficacy study, six piglets will be separated randomly into 2 groups. All pigs will be inoculated on day 0 with PRRSV strain VR-2332 with 106 TCID50/pig by oronasal inoculation, followed by IM injection (1 h later) of vehicle control (group 1) or B7 (group 2 at 10 mg or 40 mg based on the toxicity study, up to 2.5 mL in volume). Pigs will be evaluated/scored daily based on their clinical response, with body weight taken on days 0, 3, 6, 9, 12, and 14. To measure PRRSV infection, blood will be collected on day 0 and days 4, 7, 11, and 14. Viremia will be measured by qRT-PCR. All pigs will be euthanized at 2 weeks. Postmortem examinations will be performed. Pig lungs will be examined macroscopically for signs of inflammation and/or PRRSV infection. Tissue samples will be collected from each lung lobe, tracheobronchial and inguinal lymph nodes, spleen, and be frozen for viral load evaluation and hematoxylin/eosin staining. The pig lung, kidney, and liver histopathology slides will be processed and examined for toxicity evaluation.

1. Six 4-week old piglets are randomly separated into 3 groups (n=3), with Group 1 as a control, Group 2 for B7-treatment.
2. Day 0, inoculation of the pigs with PRRSV strain VR-2332 for Group 2. For Group 1 control with culture medium inoculation only.
3. Day 0, injection of drugs to pigs at 1 h after PRRSV inoculation.
4. Days 1-14 observation of pigs, blood sample collection at days 0, 4, 7, 11, and 14. Viremia will be measured by qRT-PCR from viral RNAs extracted from blood samples. Blood samples for clinical pathology will be analyzed by IDDEX Bioanalytics.
5. Day 7 necropsy: anesthesia and euthanasia will performed be as described above. At necropsy, lungs, tracheobronchial inguinal lymph nodes and spleen will be collected. The lungs and lymph nodes will be analyzed for virus load measurements, histology processing, microscopic analysis, and scoring.

What is claimed is:

1. A pharmaceutical composition comprising:

an effective amount of a PRRS virus inhibitor compound consisting essentially of:

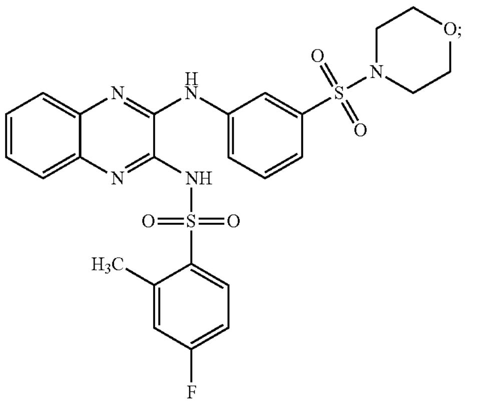 [SMILES: Cc1cc(F)ccc1S(=O)(=O)Nc1nc2ccccc2nc1Nc1cccc(S(=O)(=O)N2CCOCC2)c1]

and one or more pharmaceutically acceptable excipients.

2. The pharmaceutical composition of claim 1, wherein the pharmaceutically acceptable excipients comprise buffering agents, solubilizers, solvents, antimicrobial preservatives, antioxidants, suspension agents, a tablet or capsule diluent, or a tablet disintegrant.

3. A method for treating Porcine Reproductive Respiratory Syndrome (PRRS) by administering to a subject in need thereof an effective amount of a compound of Formula I:

(I)

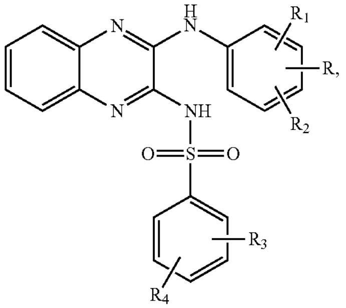

wherein:

R is

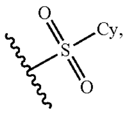

where Cy is 6- or 5-membered heterocyclyl or $C_{3-6}$ cycloalkylene, wherein Cy is unsubstituted or substituted with 1-6 substituents independently selected from $C_{1-4}$ alkyl, $C_{1-2}$ fluoroalkyl, or halogen;

$R^1$ and $R^2$ are each independently hydrogen, $C_{1-4}$ alkyl, $C_{1-2}$ fluoroalkyl, cyano, or halogen; and $R^3$ and $R^4$ are different or the same, wherein $R^3$ and $R^4$ are each independently $C_{1-4}$ alkyl, halogen, hydrogen, $C_{1-2}$ fluoroalkyl, or cyano.

* * * * *

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
aagatgacat ccggcaccac 20

<210> SEQ ID NO 2
<211> LENGTH: 22
<212> TYPE: DNA
<213> ORGANISM: Artificial Sequence
<220> FEATURE:
<223> OTHER INFORMATION: Synthetic

<400> SEQUENCE: 2
ccggcagcat aaactcaacc tg 22

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
aaaccagtcc agaggcaagg 20

<210> SEQ ID NO 4
<211> LENGTH: 23
<212> TYPE: DNA
<213> ORGANISM: Artificial Sequence
<220> FEATURE:
<223> OTHER INFORMATION: Synthetic

<400> SEQUENCE: 4
gcaaactaaa ctccacagtg taa 23

<210> SEQ ID NO 5
<211> LENGTH: 23
<212> TYPE: DNA
<213> ORGANISM: Artificial Sequence
<220> FEATURE:
<223> OTHER INFORMATION: Synthetic

<400> SEQUENCE: 5
ccctagtgag cggcaattgt gtc 23

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
ggcgcacagt atgatgcgtc 20

<210> SEQ ID NO 7
<211> LENGTH: 20
<212> TYPE: DNA
<213> ORGANISM: Artificial Sequence -continued

```
<220> FEATURE:
<223> OTHER INFORMATION: Synthetic

<400> SEQUENCE: 7

ggatggccag ccagtcaatc                                               20


<210> SEQ ID NO 8
<211> LENGTH: 24
<212> TYPE: DNA
<213> ORGANISM: Artificial Sequence
<220> FEATURE:
<223> OTHER INFORMATION: Synthetic

<400> SEQUENCE: 8

tgacgtcatc ttcagtcgct agag                                          24


<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9

catcctgggc tacactgagg                                               20


<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10

gcttgacgaa gtggtcgttg                                               20
```